United States Patent [19]

Varma et al.

[11] Patent Number: 4,654,367
[45] Date of Patent: Mar. 31, 1987

[54] HYDROXAMIC ACIDS OF 7-OXABICYCLOHEPTANE SUBSTITUTED ETHERS USEFUL AS ANTI-ALLERGY AND ANTI-INFLAMMATION AGENTS

[75] Inventors: Ravi K. Varma, Belle Mead; Jagabandhu Das, Plainsboro, both of N.J.

[73] Assignee: E. R. Squibb & Sons, Inc., Princeton, N.J.

[21] Appl. No.: 829,257

[22] Filed: Feb. 14, 1986

[51] Int. Cl.$^4$ .................. C07D 307/00; A61K 31/34; A61K 31/557
[52] U.S. Cl. ..................................... 514/469; 549/463
[58] Field of Search ......................... 549/463; 514/469

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |

FOREIGN PATENT DOCUMENTS 0043292 8/1982 European Pat. Off. .
0082646 6/1983 European Pat. Off. .
2039909 8/1980 United Kingdom .

Primary Examiner—Henry R. Jiles
Assistant Examiner—Bernard I. Dentz
Attorney, Agent, or Firm—Lawrence S. Levinson; Burton Rodney

[57] ABSTRACT

Hydroxamic acids of 7-oxabicycloheptane substituted ether prostaglandin analogs are provided having the structural formula

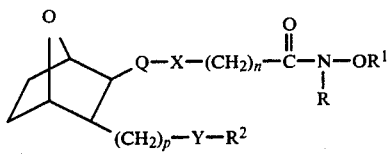

wherein Q is —CH$_2$—A—(CH$_2$)$_n$—; X is S or O, Y is O or

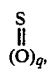

and including all stereoisomers thereof.

The compounds are inhibitors of Δ$^5$-lipoxygenase and inhibitors of prostaglandin and leukotriene biosynthesis and as such are useful, for example, as anti-allergy and antiinflammatory agents and also as antipsoriatic agents.

20 Claims, No Drawings

HYDROXAMIC ACIDS OF 7-OXABICYCLOHEPTANE SUBSTITUTED ETHERS USEFUL AS ANTI-ALLERGY AND ANTI-INFLAMMATION AGENTS

DESCRIPTION OF THE INVENTION

The present invention relates to hydroxamic acid of 7-oxabicycloheptane substituted ethers which are inhibitors of $\Delta^5$-lipoxygenase and inhibitors of prostaglandin and leukotriene biosynthesis and as such are useful, for example, as anti-allergy and antiinflammatory agents and also as antipsoriatic agents. These compounds have the structural formula

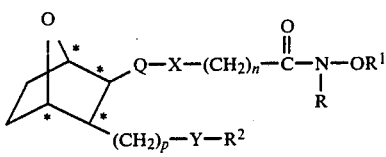

I and including all stereoisomers thereof, wherein

Q is $-CH_2-A-(CH_2)_m$ wherein A is $-CH=CH-$ or $-(CH_2)_2$, m is 1 to 6 wherein A is $-CH=CH-$ and m is 0 to 6 wherein A is $(CH_2)_2$; X is S or O; n is 1 to 4; R is H, lower alkyl, aryl, aralkyl or cycloalkyl; $R^1$ is H, lower alkyl, aryl, aralkyl, cycloalkyl, alkanoyl or aroyl; p is 1 to 5; Y is O or $S(O)_q$ wherein q is 0, 1 or 2; and $R^2$ is lower alkyl, aryl, aralkyl, cycloalkyl, cycloalkylalkyl, lower alkenyl or lower alkynyl.

Thus, the compounds of the invention include the following types of compounds:

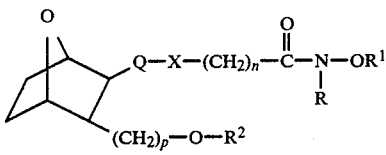

IA

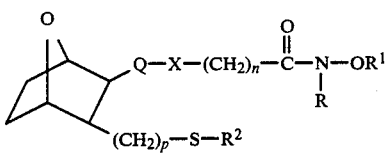

IB

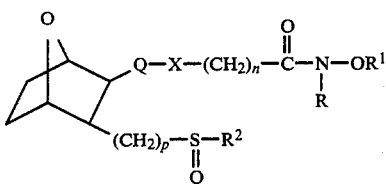

IC

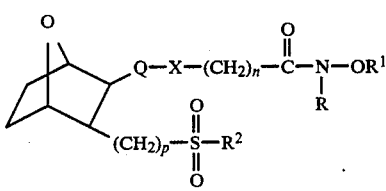

ID

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), and/or 1 or 2 lower alkoxy groups.

The term "aralkyl", "aryl-alkyl" or "aryl-lower alkyl" as used herein by itself or as part of another group refers to lower alkyl groups as discussed above having an aryl substituent, such as benzyl.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The terms "alkanoyl" and "aroyl" refer to a lower alkyl group linked to a carbonyl group or an aryl group linked to a carbonyl group.

The term "halogen" or "halo" as used herein by itself or as part of another group refers to chlorine, bromine, fluorine or iodine, with chlorine being preferred.

The terms "$(CH_2)_m$", "$(CH_2)_n$" and "$(CH_2)_p$" include a straight or branched chain radical having 1 to 7 carbons in the normal chain in the case of "$(CH_2)_n$" and 1 to 7 carbons in the normal chain in the case of "$(CH_2)_m$" and "$(CH_2)_p$" and may contain one or more lower alkyl and/or halogen substituents. Examples of $(CH_2)_m$, $(CH_2)_n$ and $(CH_2)_p$ groups include

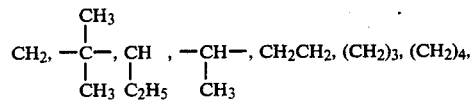

-continued

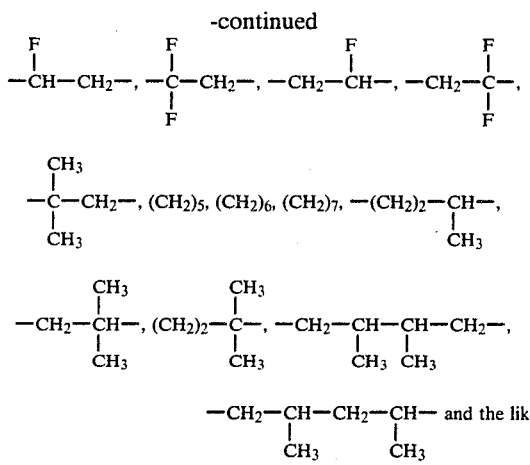

Preferred are those compounds of formula I wherein Q is —CH$_2$—A—(CH$_2$)$_m$—, A is —CH=CH— or —CH$_2$—CH$_2$—, m is 1 to 3, X is O, n is 1 to 3, p is 1, Y is O or S, R is alkyl, R$^1$ is H, and R$^2$ is lower alkyl, such as hexyl, aryl, such as phenyl, or aralkyl such as benzyl.

The various compounds of the invention may be prepared as outlined below.

Compounds of the invention wherein Q is —CH$_2$—CH=CH—(CH$_2$)$_m$, m is 1 to 6, X is O, n is 1 to 4, p is 1 and Y is O may be prepared by reducing the mesoanhydride A

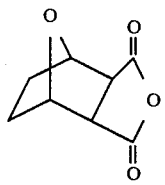

A by treating A with lithium aluminum hydride in the presence of an inert solvent such as tetrahydrofuran to form the diol B

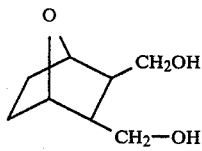

B

Diol B is then treated with a base such as sodium hydride in the presence of a solvent such as dimethylformamide and then is reacted with sulfonate reactants C, that is mesyl-OR$^2$ or C', that is, tosyl-OR$^2$ or halide C'', that is R$^2$Hal to form the ether alcohol II

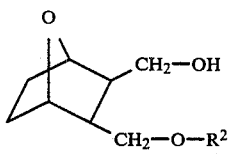

II which is treated with tosyl chloride in the presence of methylene chloride, pyridine and lithium chloride to form the chloride III

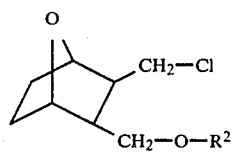

III

Chloride III is then treated with sodium cyanide in the presence of an inert solvent such as dimethyl sulfoxide at elevated temperatures of 90° to 95° C. to form the cyano compound IV

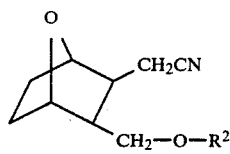

IV

The cyano compound IV in toluene at reduced temperatures of −78° C. to 0° C. under argon is treated with diisobutylaluminum hydride to form the aldehyde V

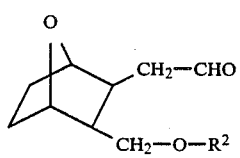

V

Employing the Wadsworth-Emmons procedure, aldehyde V is added to a solution of phosphonate D

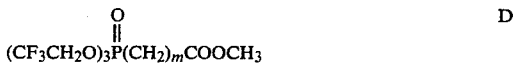

D

18-Crown-6, and potassium hexamethyl silyl amide in tetrahydrofuran to form the ester VI (where m=0)

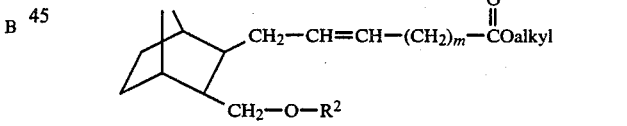

VI which is dissolved in inert solvent such as toluene and reduced by treatment with diisobutyl aluminum hydride at reduced temperatures of −78° to 0° C. under argon to form alcohol VII (where m is 1 to 6).

Alternatively, the phosphonium salt E

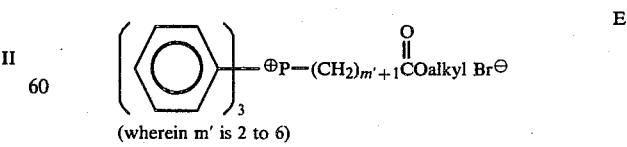

E (wherein m' is 2 to 6)

is reacted with the aldehyde V in the presence of bases like potassium t-amylate, potassium t-butoxide, n-butyl lithium, etc. to form the ester VI (where m is 1 to 6) which is then reduced with diisobutyl aluminum hydride as above to the alcohol VII (where m=1 to 6)

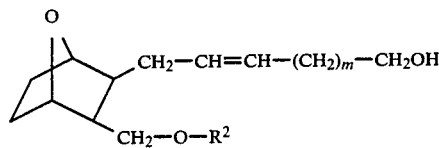

VII

The alcohol VII is then reacted in dichloromethane with bromo compound F

Br(CH2)nCOOalkyl            F in the presence of a phase transfer catalyst like tetrabutyl ammonium sulfate and base such as aqueous sodium hydroxide under argon to form ester VIII

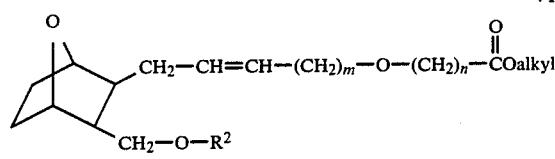

VIII which is hydrolyzed by treatment with lithium hydroxide to form acid IX

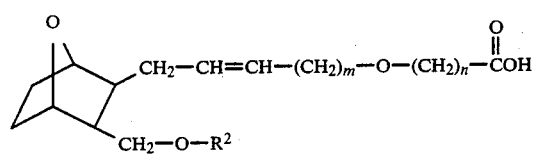

IX

Acid IX may then be converted to the corresponding hydroxamate

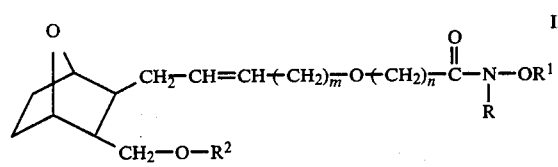

IE employing procedures as set out hereinbefore.

Compounds of Formula I wherein Q is —CH2—CH2—CH2—(CH2)m—, m is 0 to 6, X is O, n is 1 to 4, p is 1 and Y is O, that is

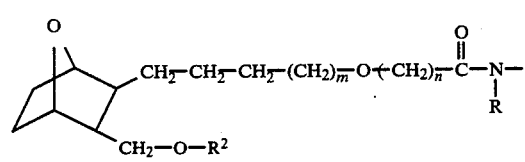

IF may be prepared by hydrogenating ester VI

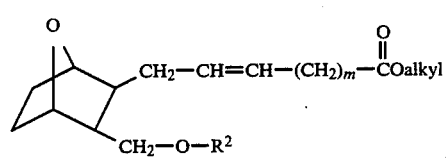

VI by treating VI dissolved in dry methanol, with hydrogen in the presence of palladium on carbon to form the ester X

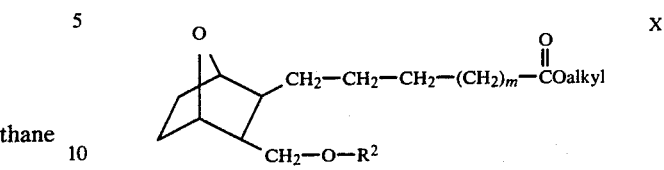

X which is then reduced by treating with lithium aluminum hydride in the presence of tetrahydrofuran under argon to form the alcohol XI

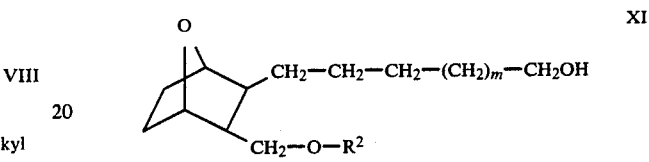

XI

The alcohol XI is then treated with bromo compound F in the presence of tetrabutyl ammonium sulfate and base such as aqueous sodium hydroxide under argon to form ester XII

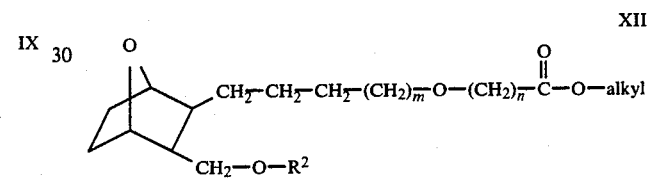

XII which is then hydrolyzed by treatment with sodium hydroxide (or lithium hydroxide) to form acid XIII

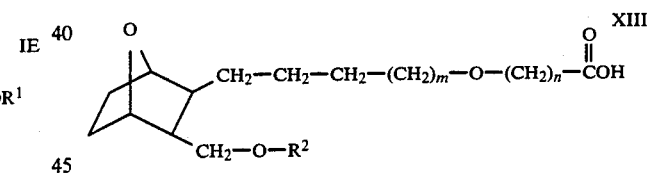

XIII

Acid XIII may then be converted to the corresponding hydroxamate IF

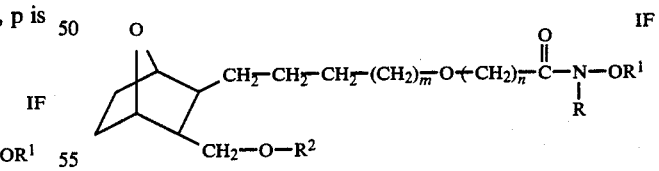

IF employing procedures as set out hereinbefore.

Compounds of formula I wherein Q is —CH2—CH2)2—(CH2)m—, X is S, n is 1 to 4, m is 1, p is 1 and Y is O may be prepared from alcohol XI

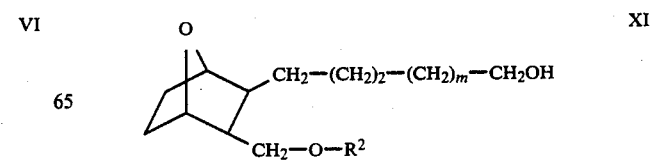

XI as follows.

Aldehyde V is treated with a reaction medium formed of sodium hydride or other base such as sodium methoxide or potassium t-butoxide, suspended in dry tetrahydrofuran, and a phosphonate of the structure

(CH₃O)₂P(O)CH₂COOCH₃    G to form the ester XIV

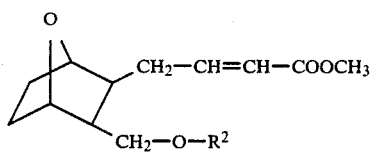
XIV

Ester XIV is then dissolved in methanol and reduced by treatment with hydrogen in the presence of a palladium on carbon catalyst to form the saturated ester XV

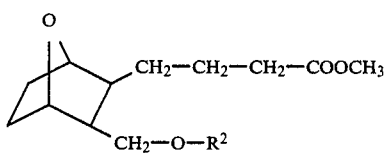
XV which is then further reduced by treatment with lithium aluminum hydride or other reducing agent in the presence of an inert solvent such as tetrahydrofuran to form the alcohol XVI

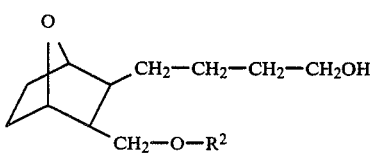
XVI

The alcohol XVI is then subjected to a modified Mitsonubu reaction wherein a mixture of the alcohol XVI and thiolacetic acid in an inert solvent such as tetrahydrofuran, ether or toluene is reacted with a mixture of triphenylphosphine and diisopropylazadicarboxylate in an inert solvent such as tetrahydrofuran at reduced temperatures of from about 0° to about 25° C. to form thioacetate XVII

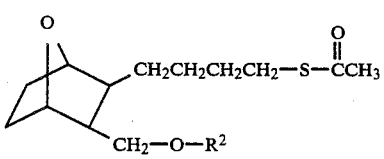
XVII

Thioacetate XVII is then reduced by treating with lithium aluminum hydride or diborane in the presence of an inert organic solvent such as tetrahydrofuran or ether to form the thiol XVIII

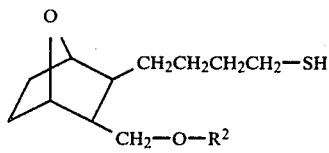
XVIII

Thiol is then alkylated by reacting with alkylating agent H

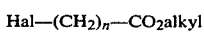
Hal—(CH₂)ₙ—CO₂alkyl    H in the presence of a base such as sodium or potassium carbonate and an inert solvent such as acetone, tetrahydrofuran or dimethylformamide to form ester XIX

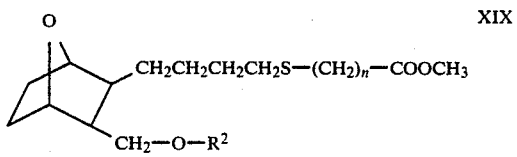
XIX which is then hydrolyzed by treatment with alkali metal hydroxide such as sodium or lithium hydroxide, to form the acid XX

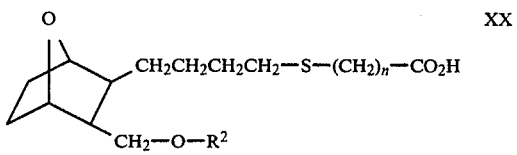
XX

The acid XX may then be converted to the hydroxamate IG

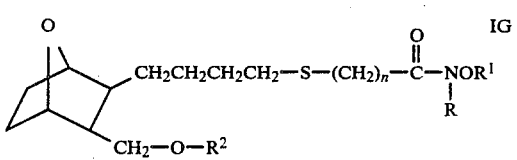
IG employing procedures as set forth hereinbefore.

The 7-oxabicycloheptane ether compounds of formula I of the invention wherein X is O, Q is CH₂CH₂CH₂(CH₂)ₘ, m is 1 to 6, p is 1, Y is S and n is 1 to 4

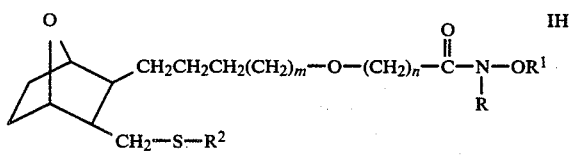
IH may be prepared starting with the cyanoalcohol XXI

XXI which is subjected to a benzylation wherein compound XXI is reacted with a base such as NaH, NaOCH₃, KH, KOt—C₄H₉ and the like in the presence of an inert solvent, such as dimethylformamide, dimethylsulfoxide, dimethoxyethane or tetrahydrofuran to form the mono benzylether compound XXII

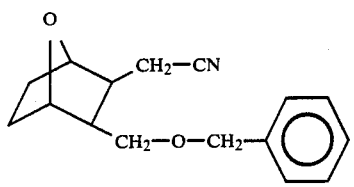

XXII

Compound XXII is reduced with diisobutyl aluminum hydride in the presence of an inert solvent, such as tetrahydrofuran, toluene or methylene chloride, to form the aldehyde XXIII

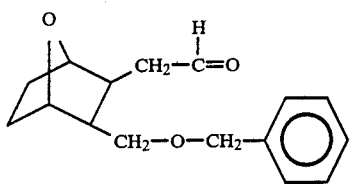

XXIII

Aldehyde XXIII is then made to undergo a Wadsworth-Emmons reaction (employing the procedure set out above with respect to the conversion of aldehyde V to VI) to form the ester XXIV

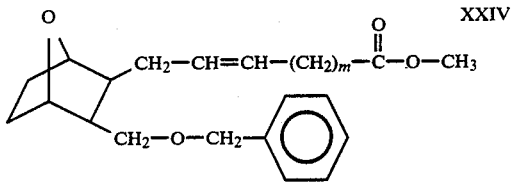

XXIV which is reduced with diisobutyl aluminum hydride in the presence of toluene at reduced temperatures of from −78° to 0° C. to form the alcohol XXV

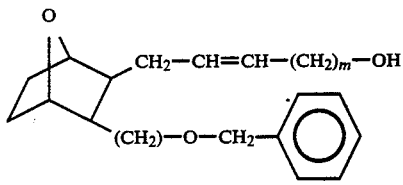

XXV

Alcohol XXV is then treated with tetrabutyl ammonium sulfate and an alkylating agent I

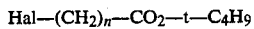

I in the presence of aqueous base such as sodium or potassium hydroxide and dichloromethane to form the ester XXVI

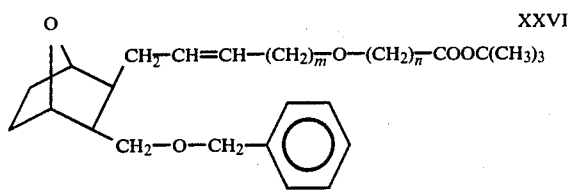

XXVI which is then reduced by treatment with hydrogen in the presence of methanol and palladium on carbon catalyst to form the alcohol XXVII

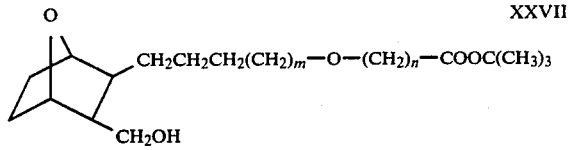

XXVII

Alcohol XXVII is then subjected to a modified Mitsonubu reaction as described hereinbefore by treating a mixture of alcohol and thiolacetic acid in an inert solvent such as tetrahydrofuran with a mixture of triphenylphosphine and diisopropylazadicarboxylate to form the thiolacetate XXVIII

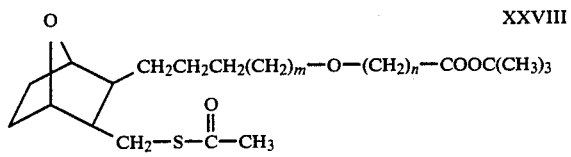

XXVIII

Thiolactate XXVIII is then reacted with a halide C″

C″ in the presence of a base such as potassium carbonate and alcohol solvent such as methanol to form the ester XXIX

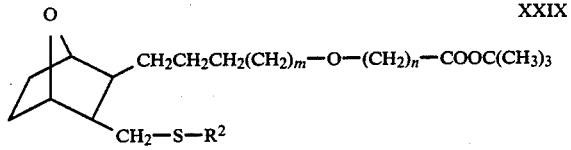

XXIX which is then treated with an acid such as trifluoroacetic acid in the presence of an inert solvent such as methylene chloride preferably in the presence of anisole to form the acid XXX

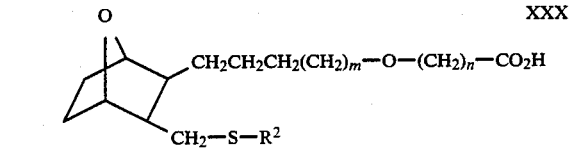

XXX

Acid XXX may then be converted to the hydroxamate IH employing procedures as set out hereinbefore.

Compounds of formula I wherein Q is CH₂—(CH₂)₂—(CH₂)ₘ and m is 0, X is O or S and Y is O or S, that is,

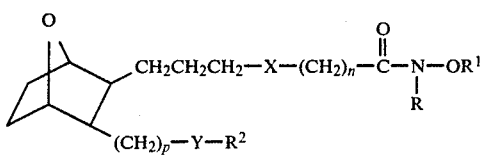

may be prepared by subjecting aldehyde XXIII

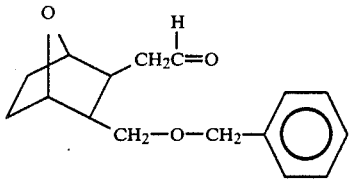

to a Wittig reaction by reacting aldehyde XXIII with an alkoxymethyltriphenylphosphonium halide, such as (methoxymethyl)triphenylphosphonium chloride and a base like potassium t-amylate to form the aldehyde

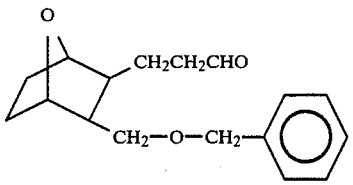

Aldehyde XXXI is then reduced by treatment with sodium borohydride to form the alcohol XXXII

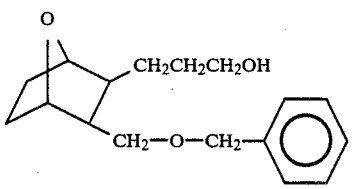

Alcohol XXXII may then be treated with appropriate alkylating agent J

Hal(CH$_2$)$_n$—CO$_2$t—butyl   J in the presence of sodium or potassium hydroxide to form the ester XXXIII

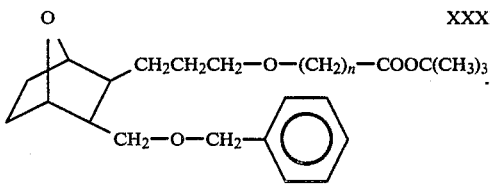

The ester XXXIII may then be employed to prepare compounds of the invention wherein m is O, and X is O or S and Y is O or S employing procedures as set out hereinbefore for preparing compounds wherein m is other than 1.

Compounds of formula I wherein Q is CH$_2$—(CH$_2$)$_2$—(CH$_2$)$_m$ and m is 2 to 6 and X is S and Y is O, that is

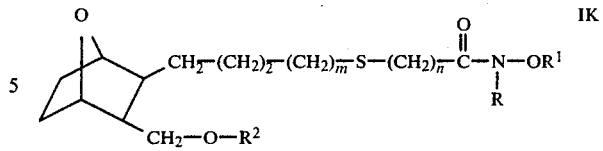

may be prepared by reducing ester XXXIV

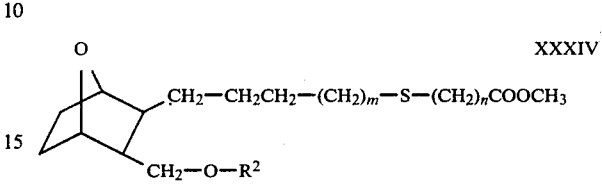

by treatment with lithium aluminum hydride to form the alcohol XXXV

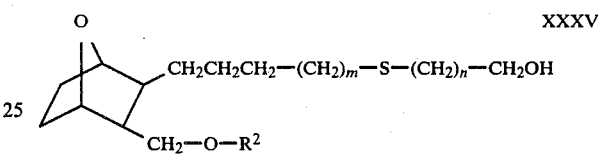

Alcohol XXXV is then subjected to a modified Mitsonubu reaction to form the corresponding thioacetate XXXVI

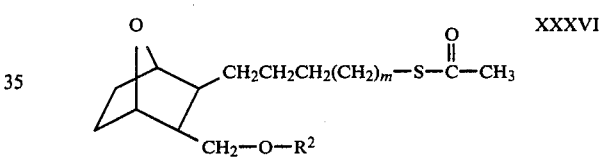

Thioacetate XXXVI is reduced by treatment with lithium aluminum hydride to form the thiol XXXVII

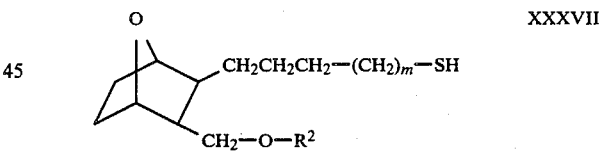

which is then alkylated by reaction with J

Hal(CH$_2$)$_n$CO$_2$t-butyl   J as described above to form ester XXXVIII

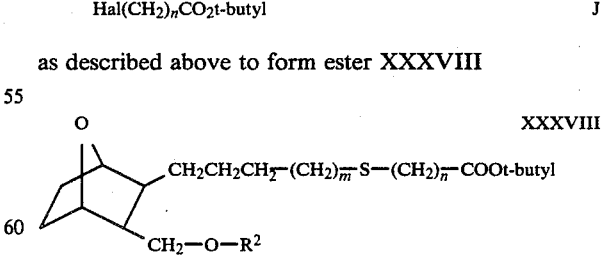

Ester XXXVIII is then converted into the corresponding acid which is then converted to the hydroxamate IK as described above.

Compounds of the invention wherein X is S, Q is CH$_2$CH$_2$CH$_2$(CH$_2$)$_m$ wherein m is 1 to 6, p is 1, Y is S and n is 1 to 4, that is

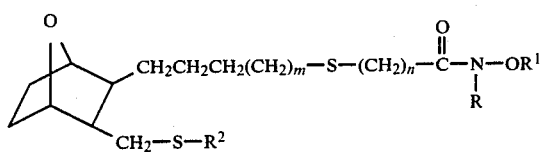

may be prepared starting with the alcohol XXXIX

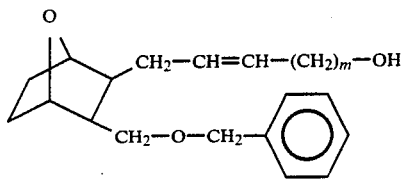

which is reduced by treatment with hydrogen in the presence of methanol and palladium on carbon catalyst to form the diol XL

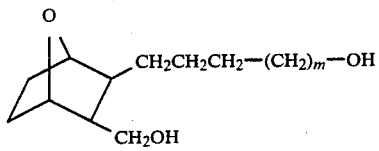

Diol XL is then subjected to a modified Mitsonubu reaction by treating with diisopropylazadicarboxylate, triphenylphosphine and thiolacetic acid as described hereinbefore to form the alcohol XLI

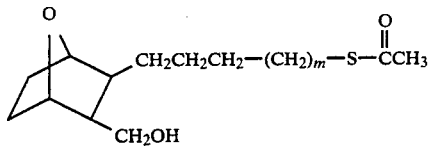

which is then reduced by treatment with lithium aluminum hydride in the presence of an inert solvent such as tetrahydrofuran to form thiol XLII

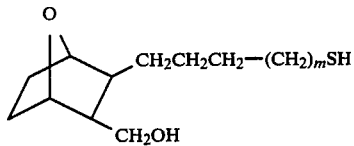

Alcohol XLII is then treated with alkylating agent J

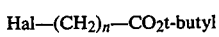

in the presence of a base such as potassium carbonate and methanol to form alcohol XLIII

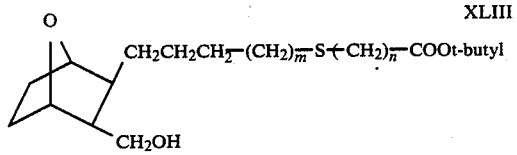

The alcohol XLIII is subjected to a modified Mitsonubu reaction as described above to form the thiolacetate XLIV

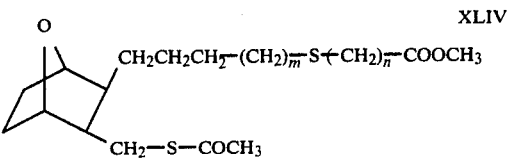

The thiolacetate XLIV is then treated with halide C″

in the presence of a base such as potassium carbonate and methanol to form the thio ester XLV

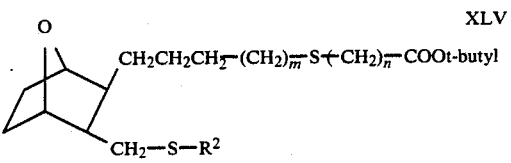

which is converted by reaction with trifluoroacetic acid as described hereinbefore to the corresponding acid XLVI

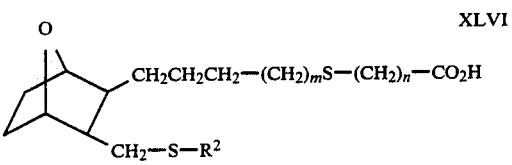

Acid XLVI is then converted to the hydroxamate IL employing procedures as described above.

Compounds of formula I wherein Q is —CH$_2$CH=CH(CH$_2$)$_m$—, m is 2 to 6, X is S and Y is O, that is compounds of the structure IM

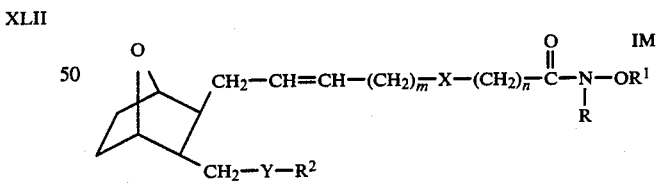

may be prepared by subjecting alcohol VII

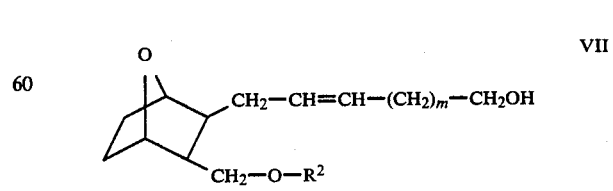

(wherein m is 1 to 6)

to a modified Mitsonubu reaction as described hereinbefore to form thioacetate XLVII

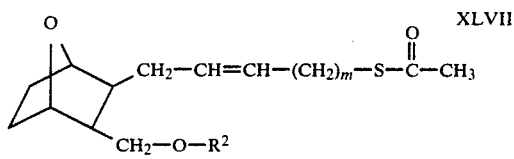

XLVII which is then reduced by treatment with lithium aluminum hydride to form the thiol XLVIII

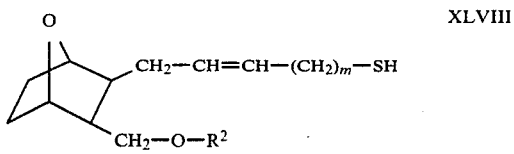

XLVIII

Thiol XLVIII is alkylated by reaction with J

Hal(CH$_2$)$_n$—CO$_2$t-butyl      J as described above to form ester XLIX

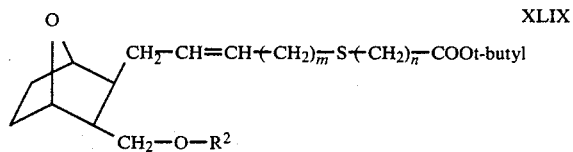

XLIX

Ester compound XLIX is then converted into the corresponding acid L

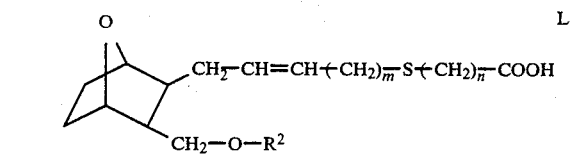

L which is then converted to the hydroxamate IM as described above.

Compounds of formula I wherein Q is —CH$_2$—CH=CH—(CH$_2$)$_m$—, m is 1 to 6, X is S, n is 1 to 4, p is 1 and Y is S, that is

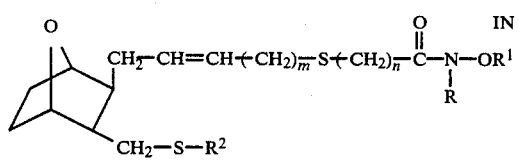

IN may be prepared by treating K

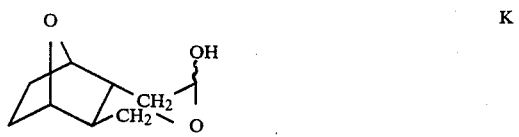

K (described in U.S. Pat. No. 4,143,054) with a Wittig reagent of the structure

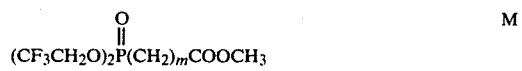

M in the presence of a base such as potassium hexamethyl silylamide and 18-Crown-6 in the presence of an inert solvent such as tetrahydrofuran to form the alcohol LI

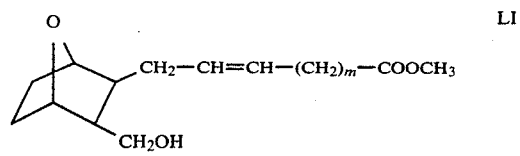

LI

The alcohol LI is then subjected to a modified Mitsonubu reaction wherein a mixture of the alcohol LI and thiolacetic acid in an inert solvent such as tetrahydrofuran, ether or toluene is reacted with a mixture of triphenylphosphene and diisopropylazadicarboxylate in an inert solvent at reduced temperatures of from about 0° to about 25° C. to form thioacetate LII

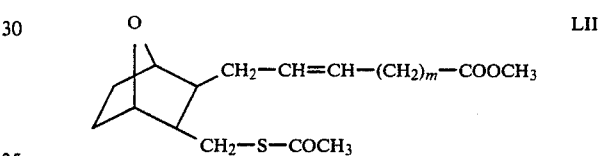

LII

Thioacetate LII is then reacted with halide C'', mesyl-OR$^2$ (C) or tosyl-OR$^2$ (C') in the presence of methanol and base such as potassium carbonate to form the thioether LIII

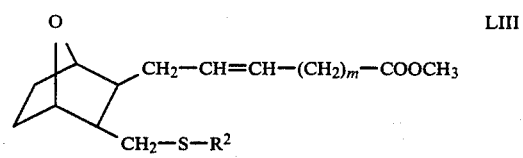

LIII

Thioether LIII is then reduced by treatment with diisobutyl aluminum hydride (DIBAL-H) at reduced temperatures (−78° to 0° C.) in the presence of an inert solvent such as toluene, or tetrahydrofuran to form the alcohol LIV

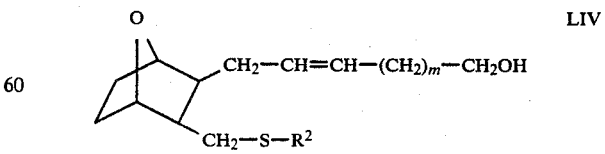

LIV

The alcohol LIV is then subjected to a modified Misonubu reaction, as described above with respect to the conversion of alcohol VII to thioacetate XLVII, to form the thioacetate LV

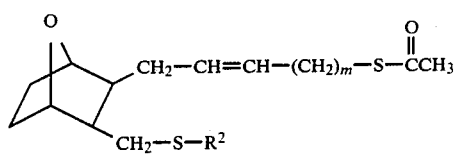
LV

The thioacetate LV is then alkylated by reacting with alkylating agent J

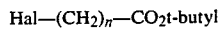
J in the presence of base such as potassium or sodium carbonate and methanol to form thioether LVI

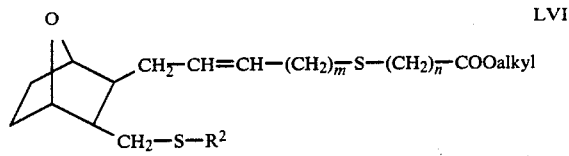
LVI which is then hydrolyzed by treatment in methylene chloride with trifluoroacetic acid to form the acid LVII

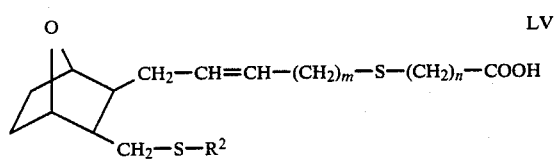
LVII

The acid LVII may then be converted to the hydroxamate IN employing procedures as set forth hereinbefore.

Compounds of formula I wherein Q is —CH$_2$—CH=CH—(CH$_2$)$_m$—, m is 1 to 6, X is O, n is 1 to 4, p is 1 and Y is S, that is compounds of the structure IO

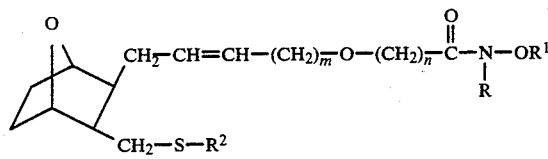
IO may be prepared starting with alcohol LIV and subjecting LIV to an alkylation by reaction with alkylating agent J,

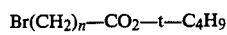
J in the presence of (C$_4$H$_9$)$_4$N$^+$HSO$_4^-$ and base and appropriate solvent such as tetrahydrofuran to form the ester LVIII

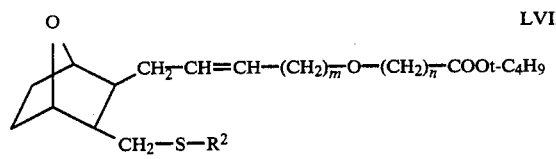
LVIII which is then reacted in methylene chloride with trifluoroacetic acid to form the acid LIX

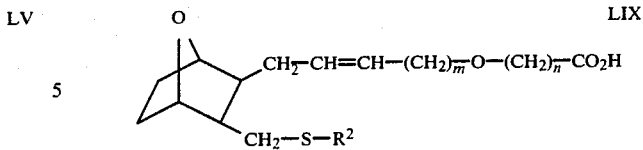
LIX

The acid LIX may then be converted to the hydroxamate IO employing procedures as set forth hereinbefore.

Compounds of the invention wherein p is 2 to 5, that is

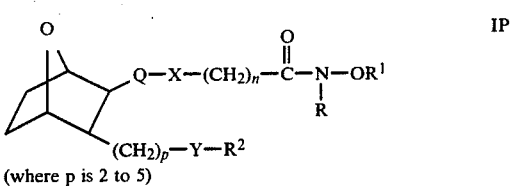
IP (where p is 2 to 5)

may be prepared as follows.
Alcohol LX or LXA

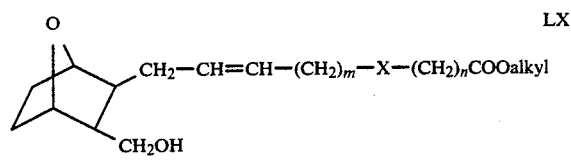
LX or

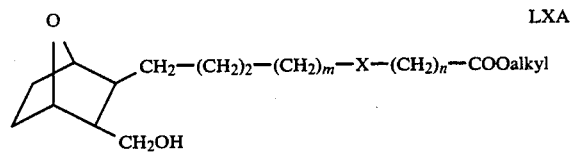
LXA is used to form the aldehyde LXI (where Q is —CH$_2$—CH=CH—(CH$_2$)$_m$—)

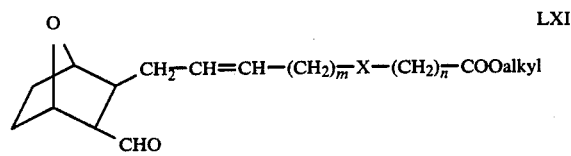
LXI or LXIA (where Q is —CH$_2$—(CH$_2$)$_2$—(CH$_2$)$_m$—)

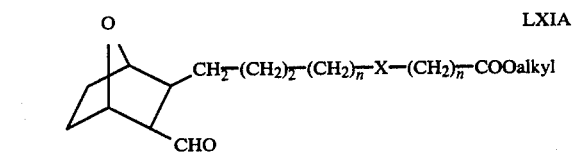
LXIA

Thus, to form aldehyde LXI where Q is —CH$_2$—CH=CH—(CH$_2$)$_m$—, compound LX is subjected to a Collins oxidation, for example, by reacting LX with chromium trioxide pyridine complex. To form the aldehyde LXIA (where Q is —CH$_2$—(CH$_2$)$_2$—(CH$_2$)$_m$—) compound LX is reduced, for example, with hydrogen over a palladium on carbon catalyst, to form hydroxymethyl compound LXA (where Q is CH$_2$—CH$_2$—CH$_2$—(CH$_2$)$_m$) and compound LXA is subjected to a Collins oxidation to form aldehyde LXIA (where Q is $CH_2-(CH_2)_2-(CH_2)_m$). The aldehyde LXI or LXIA is used to prepare aldehyde LXII

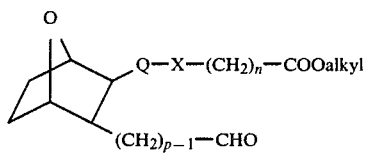

LXII (where p is 2-5) by carrying out a homologation sequence, such as a Wittig reaction with $(C_6H_5)_3P=CHOMe$ followed by hydrolysis, (p-1) times. The aldehyde LXII (where p is 2 to 5) is then carried on to compounds of this invention where p is 2 to 5, that is, IP

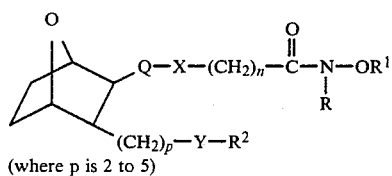

IP (where p is 2 to 5)

by reducing aldehyde LXII by reacting with a reducing agent such as sodium borohydride to form alcohol LXIII

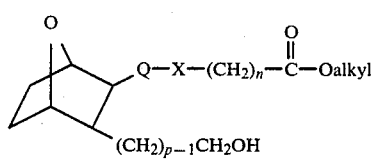

LXIII

The alcohol LXIII may then be employed to form the various compounds of the invention employing procedures as set out hereinbefore.

The compounds of the invention are $\Delta^5$-lipoxygenase inhibitors and prevent prostaglandin and leukotriene $C_4$ formation in macrophages (Samuelsson, B., Science, Vol. 220, p. 568-575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma. In addition, the compound of the invention are useful as antipsoriatic agents.

The compounds of the invention as well as the acid precursors thereof are also arachidonic acid cyclooxygenase inhibitors and are useful as antiinflammatory agents in the manner of indomethacin, aspirin and phenylbutazone as indicated by carragenin-induced edema in the rat [Ref: Winter et al, J. Pharmacol, Exp. Ther. 141: 369, 1963] and they may be used to decrease joint swelling, tenderness, pain and stiffness in conditions such as rheumatoid arthritis.

An effective but essentially non-toxic quantity of the compound is employed in treatment.

The compounds of the invention can be administered orally or parenterally to various mammalian species known to be subject to such maladies, e.g., humans, cats, dogs, and the like in an effective amount within the dosage range of about 0.1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the present invention. Unless otherwise indicated, all temperatures are expressed in degrees Centigrade.

EXAMPLE 1

[1α,2β(Z),3β,4α]-2-[[4-[3-[(Hexyloxy)methyl]-7-oxabicyclo[2.2.1]hept-2-yl]-2-butenyl]oxy]-N-hydroxy-N-methylacetamide A. (1α,2β,3β,4α)-3-[(Hexyloxy)methyl]-7-oxabicyclo[2.2.1]hept-2-yl acetaldehyde (1) (1α,2β,3β,4α)-exo-7-oxabicyclo[2.2.1]heptane-2,3-dimethanol To a suspension of 11.4 g lithium aluminum hydride (300 mmole) in 400 ml of dry THF at 0° C. was added dropwise a solution of 32 g cis-exo 7-oxabicyclo[2.2.1]heptane-2,3-dicarboxylic anhydride (prepared as described in U.S. Pat. No. 4,143,054) (190 mmole) in 400 ml of dry THF over a period of 1 hour. The reaction mixture was stirred at 25° C. for 18 hours, cooled to 0° C. and quenched by slow addition of a saturated $Na_2SO_4$ solution, and filtered. The solid was washed with three 100 ml portions of $CH_2Cl_2$. The combined organic layer was dried over $MgSO_4$ and concentrated to give 32 g of title diol as a colorless solid.

(2) (1α,2β,3β,4α)-3-[(Hexyloxy)methyl]-7-oxabicyclo[2.2.1]heptane-2-methanol

A suspension of 50% sodium hydride (16.7 g of 0.35 mmole; prewashed with ether) in dry dimethylformamide (350 ml) was cooled down to 0° under $N_2$ and treated dropwise with a solution of the Part (1) diol (50 g.; 0.316 mole) in dry dimethylformamide (150 ml). The reaction mixture was stirred at 0° for 30 minutes and at room temperature for 30 minutes after which n-hexylbromide (59.8 ml or 70.3 g; 0.42 mmole) was added. The mixture was then stirred at room temperature for 15 minutes, at 120° (oil bath) for 15 hours, cooled and quenched with a 25% ammonium chloride solution (300 ml). The resulting suspension was extracted three times with ether (1.0 liter), the organic extracts were dried (anhydrous $MgSO_4$), filtered and evaporated to a syrup (90.0 g). The crude product mixture was chromatographed (gravity) on a silica gel column (Woelm; 1.2 kg), eluting the column with EtOAc-hexane (1:4, 24.3 liters). The desired fractions were combined and evaporated to give 26.94 g of homogeneous (tlc) title compound. An additional 28.7 g of the desired compound containing a trace of another component was obtained from other fractions giving a total yield of 72.6%. An analytical sample was obtained by distilling 1.0 g of material on a Buchi GKR-50 apparatus, at 225° and 0.4 mm.

$H$-NMR (270 MHz, CDCl$_3$): δ 0.89 (t, 3H, J=~8, H$_{21}$); 1.29-1.7 (m, 12H); 2.2 (m, 2H, J=~4, H$_8$+H$_{13}$); 3.3-3.80 (m, 7H, - - - , H$_7$, H$_{14}$+H$_{16}$); 4.23 (d, 1H, J=~2, H$_9$); 4.29 (d, 1H, J=~2, H$_{12}$) ppm.

Anal Calcd for C$_{14}$H$_{26}$O$_3$: C, 69.38; H, 10.81. Found: C, 69.36; H, 10.60.

(3) (1α,2β,3β,4α)-2-Chloromethyl-3-[(hexyloxy)methyl]-7-oxabicyclo[2.2.1]heptane 5.0 g (20.6 mole) of (1α,2β,3β,4α)-3-(hexyloxy)methyl-7-oxabicyclo[2.2.1]heptane-2-methanol, 4.73 g (24.8 mmole) of p-toluenesulfonylchloride, 873 mg (20.6 mmole) of lithium chloride and 3.3 ml of dry pyridine were stirred together in dichloromethane (15 ml) at room temperature under nitrogen for 24 hours. The reaction mixture was partitioned between ether (250 ml) and saturated sodium chloride solution (20 ml). The aqueous phase was re-extracted with ether (250 ml), the combined organic extracts were dried (anhydrous MgSO$_4$), filtered and the clear filtrate was evaporated down to a syrup (5.3 g). The crude product was flash chromatographed on a silica gel column (LPS-1), eluting the column with Et$_2$O:hexane (1:9, 6.0 liters) and Et$_2$O:hexane (1:1, 6.0 liters). The fractions containing the desired product were combined and evaporated to give 3.35 g (62.4%) of the title chloro compound as a homogeneous (tlc) oil with consistent H$^1$ and C$^{13}$ spectral data.

(4) (1α,2β,3β,4α)-2-Cyanomethyl-3-[(hexyloxy)methyl]-7-oxabicyclo[2.2.1]heptane

A solution of Part (3) compound (3.35 g, 12.8 mmole) and sodium cyanide (1.29 g) in dry dimethylsulfoxide (4.6 ml) was heated at 90°-95° (oil bath) under argon for 19 hours with stirring. The mixture was cooled to room temperature, diluted with water (12 ml) and extracted twice with ether (75 ml). The organic extracts were dried (anhydrous MgSO$_4$), filtered and the clear filtrate concentrated in vacuo to a light yellow oil (3.18 g).

This oil was flash chromatographed on a silica gel column (LPS-1), eluting the column with Et$_2$O:Hexane (1:2, 7.5 liters). The desired fractions were combined and concentrated to give 3.06 (95%) of the title cyano compound as a homogeneous (tlc) light yellow oil with consistent H$^1$ and C$^{13}$-NMR spectral data.

(5) (1α,2β,3β,4α)-3-([Hexyloxy)methyl]-7-oxabicyclo[2.2.1]hept-2-yl acetaldehyde 1.5 g (5.97 mmole) of the Part (4) cyano compound was dissolved in dry toluene (7.0 ml), cooled, stirred in a bath at −78° (dry ice-acetone) under argon, and treated dropwise with 5.4 ml of diisobutylaluminum hydride (25% by wt. in toluene; 9.49 mmole or 1.5 eq.). After 4 hours, the mixture was quenched at −78° with 25% NH$_4$Cl (6.0 ml), stirred for 30 minutes, warmed to about 0°, acidified with 1N HCl (16 ml), and stirred for about 30 minutes. The mixture was then extracted twice with dichloromethane (50 ml), the organic extracts were washed with saturated sodium chloride solution, (20 ml), dried (anhydrous MgSO$_4$), filtered and concentrated in vacuo to give 1.45 g (95.4%) of the title A aldehyde as a homogeneous (tlc) yellow oil with consistent H$^1$ and C$^{13}$-NMR spectral data.

B. [1α,2β(Z),3β,4α]-4-[3-[(Hexyloxy)methyl]-7-oxabicyclo[2.2.1]hept-2-yl]-2-butenoic acid, methyl ester

[Wadsworth-Emmons reaction—W. C. Still, C. Gennari, *Tetrahedron Letters*, 26, No. 41, 4405 (1983)]

A solution of bis(2,2,2-trifluoroethyl) (methoxycarbonyl methyl)phosphonate 1.3 ml, 6.02 mmole) and 18-crown-6 (5.0 g, 19 mmole) in dry THF (80 ml) was stirred in a bath at −78° under argon and 0.6M potassium hexamethyl silyl amide in THF (5.1 mmole, 8.5 ml), was added in the course of 3 minutes. After 15 minutes, a solution of the Part A aldehyde (1.0 g, 3.94 mmole) in dry THF (15 ml) was added. After 4 hours, the reaction was quenched by the addition of 25% NH$_4$Cl (35 ml). The mixture was then concentrated in vacuo to remove most of the THF, and was extracted with Et$_2$O (2×100 ml). The extracts were combined, washed with brine, dried (MgSO$_4$ anhydrous) and evaporated to afford the crude product as an oil.[1] This was subjected to flash chromtography (silica gel, LPS-1) eluting the column with hexane-EtOAc (9:1) to isolate pure cis double bond compound (860 mg, 70.4%), a mixture of cis- and trans double bond compounds (110 mg, 9.0%) and pure trans double bond compound (130 mg, 10.6%).

[1]The H$^1$-NMR spectrum of this showed the presence of 16.4% trans and 86.3% cis double bond products.

C. [1α,2β(Z),3β,4α]-4-[3-[(Hexyloxy)methyl]-7-oxabicyclo[2.2.1]hept-2-yl]-2-butenol A solution of Part B ester (1.0 g, 3.22 mmole) in dry toluene (15 ml) was cooled and stirred in a bath at −78° under argon and a 1.5M solution of diisobutyl aluminum hydride in toluene (6.5 ml) was added. After 4.0 hours, the mixture was added under stirring into 10% HCl (25 ml) and extracted with ether (3×50 ml). The extracts were combined, washed with dilute brine, dried (MgSO$_4$ anhydrous) and evaporated to afford the homogeneous (tlc; silica gel, Et$_2$O) title compound as an oil (900 mg, 99.7%) with consistent H$^1$- and C$^{13}$-NMR spectral data. This specimen was used in the next step without further purification.

D. [1α,2β(Z),3β,4α]-2-[[4-[3-[(Hexyloxy)methyl]-7-oxabicyclo[2.2.1]hept-2-yl]-2-butenyl]oxy]acetic acid, t-butyl ester A mixture of Part C alcohol (900 mg, 3.2 mmole), t-butylbromoacetate (5.43 ml), tetrabutyl ammonium sulfate (1.7 g), THF (20 ml) and 50% NaOH (20 ml) was stirred vigorously under argon for 2.5 hours. Most of the THF was then removed in vacuo and the concentrate was extracted with CH$_2$Cl$_2$ (3×30 ml). The extracts were combined, washed with dilute brine (2×20 ml), dried (MgSO$_4$ anhydrous) and evaporated to afford the crude product as an oil. On the basis of tlc, this was a mixture of one major and two minor components in addition to impurities derived from the excess t-butylbromo acetate; the starting alcohol was absent. This mixture was flash chromatographed on a column of silica gel (LPS-1) eluting with EtOAc-hexane (1:9) to isolate homogeneous (tlc) title compound as an oil (1.16 g, 91%) with consistent H$^1$- and C$^{13}$-NMR spectral data.

E. [1α,2β(Z),3β,4α]-2-[[4-[3-[(Hexyloxy)methyl]-7-oxabicyclo[2.2.1]hept-2-yl]-2-butenyl]oxy]acetic acid A solution of Part D t-butyl ester (350 mg, 0.88 mmole) in distilled dioxane (7.0 ml) was stirred under reflux in an atmosphere of nitrogen with 2N LiOH (2.5 ml) for 1.0 hour. The mixture was then cooled to room temperature, acidified with 10% HCl (5.0 ml) and most of the dioxane was removed by concentration in vacuo. The concentrate was diluted with brine (20 ml) and extracted with ether (3×30 ml). The extracts were combined, washed with brine (2×25 ml), dried (MgSO₄ anhydrous) and evaporated to afford the product as an oil. This wash chromatographed on a column of silica gel (Baker 60–200 mesh, 15 g) eluting the column with hexane, Et₂O-hexane (3:7, 1:1), Et₂O, Et₂O—CH₃OH (1:4, 1:1), and CH₃OH. The relevant fractions were combined and evaporated. The residual oil was dissolved in Et₂O (75 ml) and was washed successively with 1.0N HCl (2×10 ml) and brine (2×10 ml) to remove silica gel. The Et₂O solution was then dried (MgSO₄ anhydrous), evaporated and dried in vacuo to afford the analytical specimen of title acid as a homogeneous (tlc) oil (235 mg, 78.4%), with consistent MS, IR (1761, 1736 cm$^{-1}$, strong, C=O), H$^1$- and C$^{13}$-NMR data.

Anal Calcd for $C_{19}H_{32}O_5$: C, 67.03; H, 9.48. Found: C, 67.04; H, 9.41.

H$^1$-NMR spectrum (FX-270, CDCl₃): δ 0.90 (t, 3H, J=~7.0, H₂₁); 2.10 (t, 3H, —, H₁₃+H₇); 3.43 (m, 4H, —, H₁₄+H₁₆); 4.10 (s, 2H, —, H₂); 4.17 (m, 2H, —, H₄); 4.26 (d, 1H, J=~4.0, H₉); 4.40 (d, 1H, J=~4.0, H₁₂); 5.62 (m, 2H, —, H₅+H₆) ppm.

F. [1α,2β(Z),3β,4α]-2-[[4-[3-[(Hexyloxy)methyl]-7-oxabicyclo[2.2.1]hept-2-yl]-2-butenyl]oxy]-N-hydroxy-N-methylacetamide A solution of Part E acid (620 mg, 1.82 mmole) and oxalyl chloride (2 ml, 22.5 mmole or 12.4 eq.) in dry benzene (10 ml) was cooled down to 0° (ice-water bath), treated with dry dimethylformamide (3 drops) and stirred at 0° for 30 minutes under nitrogen and at room temperature for 1 hour. The excess oxalyl chloride and solvent were blown off under a stream of nitrogen while heating the flask in a warm water bath and the residual oil was dried in vacuo for 1 hour. This acid chloride was dissolved in dry tetrahydrofuran (3.5 ml) and added dropwise under stirring into a cold solution (~0°, ice-water) of 98% methylhydroxylamine hydrochloride (318.7 mg, 3.74 mmole) and triethylamine (0.92 ml, 7.48 mmole) in tetrahydrofuran (4.6 ml) and water (4.6 ml). The mixture was stirred at 0° for 30 minutes, diluted with water (25 ml) and extracted twice with dichloromethane (125 ml). The combined organic extracts were washed with 1N HCl (25 ml), 5% NaHCO₃ (12 ml) and brine (20 ml), dried (anhydrous MgSO₄), filtered and evaporated to dryness giving and oil (720 mg) containing the desired product and traces of a less polar component.

This mixture was dissolved in ether (50 ml) with warming, concentrated down to a volume of ~15 ml and diluted with hexane (30 ml). The white precipitates obtained on scratching provided a homogeneous (TLC) specimen of title product[1] (524.2 mg, 77.9%) with consistent elemental analysis, MS, IR (1654 and 1636 cm$^{-1}$, strong, C=O), H$^1$- and C$^{13}$-NMR data.

[1] An additional 141.1 mg of crude product was recovered from the filtrate giving a total crude yield of 98.9%.

H$^1$-NMR Spectrum (FX-270, CDCl₃): δ 0.89 (t, 3H, J=~7, H₂₁); 1.20-2.21 (m, 16H, —, —); 3.20-3.44 (m, 7H, —, H₁₄+H₁₆+H₂₂); 3.95-4.5 (m, broad, 6H, —, H₂+H₄+H₉+H₁₂); 5.55-5.72 (m, broad, 2H, —, H₅+H₆); 8.68 (S, broad, 1H, —, N—OH) ppm.

EXAMPLE 2

(1α,2β,3β,4α)-2-[[4-[3-[(Hexyloxy)methyl]-7-oxabicyclo[2.2.1]hept-2-yl]butyl]oxy]-N-hydroxy-N-methylacetamide A. (1α,2β,3β,4α)-4-[3-[(Hexyloxy)methyl]-7-oxabicyclo[2.2.1]hept-2-yl]butanol (1) (1α,2β,3β,4α)-4-[3-[(Hexyloxy)methyl]-7-oxabicyclo[2.2.1]hept-2-yl]-2-butenoic acid, methyl ester 420 mg (8.75 mmole) of 50% NaH on paraffin was suspended in dry distilled tetrahydrofuran (60 ml), cooled down to 0° under argon and was treated dropwise with trimethylphosphonoacetate (2 ml; 12.4 mmole). The thick slurry was stirred at 0° for 30 minutes, room temperature for 1 hour and cooled back down to 0°. It was then treated dropwise with a solution of Example 1 Part A aldehyde (2.0 g; 7.86 mmole) in tetrahydrofuran (20 ml). The mixture was stirred at 0° for 30 minutes at room temperature for 2 hours and was then acidified with glacial acetic acid (2.0 ml). It was then stirred for 30 minutes, evaporated to dryness in vacuo and the resulting solid was partitioned twice between saturated NaHCO₃ solution (100 ml) and ether (400 ml). The organic phase was washed with water (200 ml), dried (anhydrous MgSO₄), filtered through a bed of silica gel (Baker; 30ml), and was evaporated to dryness to give 2.48 g (100%) of title methyl ester as an oil with a consistent $^{13}$C NMR spectrum. It was a mixture of cis and trans double bond isomers.

(2) (1α,2β,3β,4α)-4-[3-[(Hexyloxy)methyl]-7-oxabicyclo[2.2.1]hept-2-yl]butanoic acid, methyl ester 2.48 g (7.86 mmole) of Part (1) methyl ester was dissolved in dry methanol (140 ml) and hydrogenated at atmospheric pressure, at room temperature, in the presence of 5% Pd/C (420 mg) for 3 to 4 hours. The suspension was filtered and concentrated to give the title compound as a homogeneous (TLC) oil (2.49; 96.6%) with a consistent $^{13}$C spectrum which showed the absence of the double bond.

(3) (1α,2β,3β,4α)-4-[3-[(Hexyloxy)methyl]-7-oxabicyclo[2.2.1]hept-2-yl]butanol

A solution of ester compound (2) (2.1 g; 6.72 mmol) in dry tetrahydrofuran (10 ml) was added dropwise to a suspension of lithium aluminum hydride (420 mg; 11.1 mmole) in dry tetrahydrofuran (50 ml) at 0° under argon. The mixture was stirred at 0° for 30 minutes at room temperature for 3 hours, and quenched by the successive addition of water (0.42 ml), 10% NaOH (0.7 ml) and water (1.26 ml). The granular precipitates were filtered off and washed with small amounts of ether. The filtrate was diluted with ether (300 ml), dried (anhydrous MgSO₄), filtered and was concentrated to give a homogeneous (TLC) oil (1.9; 100%). This (1.4 g) was chromatographed (flash) on a silica gel column (LPS-1), eluting with Et₂O:hexane (1:1; 1.5 liters) and Et₂O:hexane (3:1, 2.0 liters) to give, after drying in vacuo, the analytical specimen of title alcohol as a clear oil (1.25 g) with consistent MS, H$^1$-NMR, C$^{13}$-NMR and IR spectral data.

Anal Calcd for $C_{17}H_{32}O_3$: C, 71.79; H, 11.34. Found: C, 71.56; H, 11.29.

$^1$H-NMR (270 MHz, CDCl₃): δ 0.91 (t, 3H, J=~9; H₂₁); 1.2–2.09 (m, 21H, —, —); 3.25–3.42 (m, 4H, —, H₁₄+H₁₆); 3.63 (t, 2H, J=~6, H₄); 4.28 (d, 1H, J=~4, H₉); 4.40 (d, 1H, J=~4, H₁₂) ppm.

B. [1α,2β(Z),3β,4α]-2-[[4-[3-[(Hexyloxy)methyl]-7-oxabicyclo[2.2.1]hept-2-yl]butyl]oxy]acetic acid, t-butyl ester A solution of 500 mg (1.76 mmole) of Part A alcohol in 50% NaOH (10.3 ml) and tetrahydrofuran (10.3 ml) was treated with t-butybromoacetate (2.84 ml, 17.6 mmole) and tetrabutylammonium hydrogen sulfate (935 mg, 2.75 mmole) and stirred under argon at room temperature for 20 hours. The organic solvent was evaporated off and the resulting slurry diluted with water (27.5 ml). The aqueous solution was acidified with 10% HCl (~25 ml) and extracted twice with dichloromethane (125 ml). The organic phase was washed with water (50 ml), dried (anhydrous MgSO$_4$) and evaporated to dryness. The residual syrup was chromatographed (flash) on a silica gel column (LPS-1), eluting the column with Et$_2$O:hexane (1:4, 4.0 liters), Et$_2$O:hexane (1:1, 4.0 liters) and Et$_2$O:hexane (4:1, 3.0 liters). The desired fractions were combined to give the title ester compound as a homogeneous (TLC) oil (381.4 mg, 84.1%) with a consistent H$^1$-NMR-spectrum.

C. [1α,2β(Z), 3β,4α]-2-[[4-[3-[(Hexyloxy)methyl]-7-oxabicyclo[2.2.1]hept-2-yl]butyl]oxy]acetic acid A solution of Part B ester (314.9 mg, 0.79 mmole) in tetrahydrofuran (3.16 ml) and 50% NaOH (3.16 ml) was stirred at room temperature under argon for 19 hours. A solution of the impure product (~39 mg) from a previous run in tetrahydrofuran (0.5 ml) was combined with the reaction mixture and the entire mixture was diluted with water (40 ml) and extracted twice with ether (25 ml). The aqueous phase was acidified with 12N HCl (4 ml) and extracted twice with dichloromethane (200 ml). The organic extract was washed with a saturated sodium chloride solution (25 ml), dried (anhydrous MgSO$_4$) and evaporated to give a thick oil (207.4 mg, 66.2%) which was homogeneous by TLC. This was chromatographed (gravity) on a silica gel column (Baker, 15 g), eluting the column with dichloromethane and increasing amounts of methanol in dichloromethane up to 10%. The desired fractions were combined and evaporated to dryness. In order to remove occluded silica gel, the oil obtained was dissolved in ether (75 ml) and washed with 10% HCl (10 ml), saturated NaCl (10 ml), dried (anhydrous MgSO$_4$) and concentrated to give a thick syrup (124 mg) with consistent MS, IR (the IR spectrum showed a strong C=O absorption at 1650 cm$^{-1}$ and no carboxylic acid absorption at ~3400 cm$^{-1}$ indicating strong H-bonding of the acid function), H$^1$-NMR and C$^{13}$-NMR spectra.

Anal Calcd for C$_{19}$H$_{34}$O$_5$: C, 66.63; H, 10.01. Found: C, 66.81; H, 9.90.

H$^1$-NMR spectrum (FX270; CDCl$_3$): δ 0.90 (t, 3H, J=~8, H$_{21}$); 1.21-1.70 (m, 20H, —, —); 2.03 (q, 1H, J=~7, H$_{13}$); 3.21-3.45 (m, 4H, —, H$_{14}$+H$_{16}$); 3.55 (broad s, 2H, H$_4$); 3.92 (s, 2H, —, H$_2$); 4.22 (d, 1H, J=~4, H$_9$); 4.42 (d, 1H, J=~4, H$_{12}$) ppm.

D. (1α,2β,3β,4α)-2-[[4-[3-[(Hexyloxy)methyl]-7-oxabicyclo[2.2.1]hept-2-yl]butyl]oxy]-N-hydroxy-N-methylacetamide A solution of Part C acid (640 mg, 1.87 mmole) in dry benzene (10 ml) was treated with oxalyl chloride (2 ml, 22.5 mmole) and stirred at room temperature under nitrogen for 2 hours. The excess oxalyl chloride and solvent were blown off by a stream of nitrogen while heating the flask in a warm water bath and the residual oil dried in vacuo (oil pump) for one hour. This acid chloride was dissolved in dry tetrahydrofuran (3.5 ml) and added dropwise into a cold (ice-water) solution of 98% methylhydroxylamine hydrochloride (318.7 mg, 3.74 mmole) and triethylamine (0.92 ml, 7.48 mmole) in tetrahydrofuran (4.6 ml) and water (4.6 ml). The mixture was stirred at 0° under nitrogen for 30 minutes and at room temperature for 7.0 hours, diluted with water (23 ml) and extracted twice with dichloromethane (125 ml). The organic extract was washed with 1N HCl (25 ml), 5% NaHCO$_3$ (12 ml) and brine (20 ml), dried (anhydrous MgSO$_4$), filtered and evaporated to dryness giving an oil (724 mg) containing the desired product and traces of four other components and some Part C acid.

This mixture was chromatographed (gravity) on a silica gel column (Baker, 50 ml), eluting the column with dichloromethane and CH$_2$Cl$_2$:MeOH (98:2, 95:5, 9:1, 4:1). The pure fractions (TLC) were combined to give an oil (300.8 mg)[1]. In order to remove the entrained silica gel, it was dissolved in ether (50 ml) and washed with 1N HCl (5 ml) and brine (5 ml). The organic phase was dried (anhydrous MgSO$_4$), filtered and evaporated to dryness to give the title compound as a homogeneous oil (which became a waxy solid upon standing) (300 mg) with consistent analytical, IR (1641 cm$^{-1}$, strong, C=O), mass, H$^1$- and C$^{13}$ NMR-spectral data.

[1] More title compound (117.8 mg) containing a trace of an impurity was obtained from the later fractions.

Anal calcd for C$_{20}$H$_{37}$NO$_5$: C, 64.66; H, 10.04; N, 3.77. Found: C, 64.33; H, 9.83; N, 3.43.

EXAMPLE 3

(1α,2β,3β,4α)-2-[[4-[3-[(Hexyloxy)methyl]-7-oxabicyclo[2.2.1]hept-2-yl]butyl]oxy]-N-hydroxy-N,2,2-trimethylacetamide A. (1α,2β,3β,4α)-2-[[4-[3-[(Hexyloxy)methyl]-7-oxabicyclo[2.2.1]hept-2-yl]butyl]oxy]-2-methyl acetic acid, t-butyl ester A solution of dry diisopropyl amine (0.225 ml, 1.6 mmole) in THF (20 ml), was cooled and stirred in a bath at −78° under argon and 1.65M n-BuLi in hexane (0.73 ml, 1.2 mmole) was added. After 5.0 minutes a solution of Example 2 Part B compound (400 mg, 1.0 mmole) in dry THF (5.0 ml) was added in the course of 2 minutes. After 20 minutes, a solution of dry hexamethylphosphoric triamide (HMPA) (1.0 m) in dry THF 1.0 ml) and methyl iodide (filtered through basic alumina, 4.0 mmole, 0.25 ml) were added. After 3 hours at −78°, the mixture was poured into 10% hydrochloric acid (10 ml) and concentrated in vacuo at room temperature to remove most of the THF. The concentrate was diluted with brine (25 ml) and extracted with ether (3×30 ml). The extracts were combined, washed with brine (2×10 ml), dried (MgSO$_4$ anhydrous) and evaporated to afford the crude product as an oil. This was chromatographed on a column of Silica gel (Baker 60–200 mesh, 30 g) eluting the column with hexane and Et$_2$O-hexane mixtures (1:9, 1:4, 1:1) to isolate the homogeneous (tlc) title compound as an oil (363 mg, 88%), with consistent H$^1$- and C$^{13}$-NMR spectral data.

B. (1α,2β,3β,4α)-2-[[4-[3-[(Hexyloxy)methyl]-7-oxabicyclo[2.2.1]hept-2-yl]butyl]oxy]-2-methylacetic acid, t-butyl ester A solution of dry diisopropyl amine (0.154 ml, 1.1 mmole) in dry THF (12 ml) was cooled and stirred in a bath at −78° under argon and a 1.65M solution of n-BuLi in hexane (0.61 ml, 1.0 mmole) was added. After 5 minutes, a solution of Part A compound (360 mg, 0.87 mmole) in dry THF (4.0 ml) was added in the course of 2 minutes. After 20 minutes, a solution of dry HMPA (0.5 ml) in dry THF (0.5 ml) and methyl iodide (filtered through basic alumina, 0.22 ml, b 3.5 mmole) were added. After 2 hours, the mixture was poured into 10% hydrochloric acid and concentrated in vacuo at room temperature to remove most of the THF. The concentrate was diluted with brine (20 ml) and extracted with ether (3×30 ml). The extracts were combined, washed with brine (2×10 ml), dried (MgSO4 anhydrous) and evaporated to afford the product as an oil. This was chromatographed on a column of silica gel (20 g, Baker 60–200 mesh) eluting the column with hexane and Et2O-hexane mixtures (1:9, 1:4, 1:1) to isolate the homogeneous (tlc) title compound as an oil (330 mg, 89%) with consistent $H^1$- and $C^{13}$-NMR spectral data.

C. (1α,2β,3β,4α)-2-[4-[[3-[(Hexyloxy)methyl]-7-oxabicyclo[2.2.1]hept-2-yl]butyl]oxy]-2-methylacetic acid A solution of Part B compound (315 mg, 0.74 mmole) in distilled dioxane (5.0 ml) was refluxed under stirring with 3N LiOH (3.0 ml) in an atmosphere of argon for 36 hours. The mixture was then cooled to room temperature, acidified with concentrated HCl (0.9 ml) and concentrated in vacuo to remove most of the dioxane. The concentrate was diluted with brine (20 ml) and extracted with ether (3×20 ml). The extracts were combined, washed with brine (2×20 ml), dried (MgSO4 anhydrous) and evaporated to afford crude Part C acid as an oil. A tlc examination of this (silica gel, EtOAc) revealed the presence of Part C acid and a minor more polar impurity. This was chromatographed on a column of silica gel (15 g, Baker 60–200 mesh) eluting the column with hexane, Et2O-hexane (3:7, 1:1, 7:3), Et2O, Et2O—CH3OH (95:5, 1:4, 1:1) and CH3OH. The relevant fractions were combined to isolate Part C acid and a mixture of Part C acid and the unidentified more polar component as oils.

The Part C acid thus isolated contained some silica gel. It was, therefore, dissolved in Et2O (50 ml), washed with 1N HCl (2×10 ml) and brine (2×10 ml), dried (MgSO4), evaporated and re-dried in vacuo to afford the analytical specimen as an oil (212 mg, 74%), with consistent MS, IR (1736 cm$^{-1}$, strong, C=O), $H^1$-NMR and $C^{13}$-NMR data.

Anal calcd for $C_{21}H_{38}O_5$: C, 68.07; H, 10.34. Found: C, 68.07; H, 10.25.

$H^1$-NMR spectrum (FX-270, CDCl3): δ 0.90 (t, 3H, J=~7.0, H21); 1.46 (S, 6H, —, H22+H23); 2.05 (m, 1H —, H13); 3.35 (m, 6H, —, H4+H14+H16); 4.28 (d, 1H, J=~4.0, H9); 4,42 (d, 1H, J=~4.0, H12) ppm.

D. (1α,2β,3β,4α)-2-[[4-[3-[(Hexyloxy)methyl]-7-oxabicyclo[2.2.1]hept-2-yl]butyl]oxy]-N-hydroxy-N,2,2-trimethylpropanamide A solution of Part C acid (411 mg, 1.11 mmole) in dry benzene (10 ml) was cooled and stirred in a bath at 5° and oxalyl chloride (0.5 ml) was added, followed dropwise by dry DMF (0.15 ml). Vigorous gas evolution was noted. After 30 minutes, the solvents were removed under a jet of nitrogen at ambient temperature and the residue was dried in vacuo to afford the acid chloride as an oil containing a small amount of solid (dimethyliminium chloride). This oil was dissolved in THF (2.0 ml) and added into a stirred ice-cold solution of methylhydroxylamine hydrochloride (200 mg, 2.4 mmole) and triethylamine (0.5 ml, 3.6 mmole) in 50% aqueous THF (8.0 ml). After 30 minutes, the mixture was warmed to room temperature and stirred for 4.0 hours. It was then concentrated in vacuo, the residue diluted with brine (15 ml) and 10% HCl (15 ml) and extracted with ether (3×20 ml). The extracts were combined, washed with brine, a dilute NaHCO3 solution and brine, dried (MgSO4.anhydrous) and evaporated to afford the crude product as an oil. A tlc (silica gel: 5:95 CH3OH—CH2Cl2) examination of this showed the presence of one major spot. The starting acid was absent and traces of less polar products were present. This was chromatographed on a column of silica gel (30 g, Baker 60–200 mesh) eluting the column with hexane, Et2O-hexane (1:4, 1:1) and Et2O—CH3OH (98:2) to isolate, after drying in vacuo, the analytical specimen of title compound as an oil (385 mg, 88%) with consistent IR (1631 cm$^{-1}$, strong, C=O; 3242 cm$^{-1}$, weak, OH, 1778, 1738 cm$^{-1}$, weak, C=O)[1], mass, $H^1$- and $C^{13}$-NMR spectral data.

[1]The weak C=O peaks could not be eliminated by rechromatography. The specimen was homogeneous by tlc.

Anal Calcd for $C_{22}H_{41}NO_5$: C, 66.13; H, 10.34; N, 3.50. Found: C, 66.26; H, 10.23; N, 3.36.

$H^1$-NMR Spectrum (FX-270, CDCl3)[2]: δ 0.90 (t, 3H, J=~7.0, H21); 1.48 (s, 6H, —, H22+H23); 2.02 (q, 1H, J=~4.0, H13); 3.31, 3,50 (m and broad hump respectively, 9H, H14+H16+H6+H24); 4.24 (d, 1H, J=~4.0, H9); 4.40 (d, 1H, J=~4.0, H12); 8.62 (broad s, —, —, OH) ppm.

[2]Weak singlets due to unidentified impurities were present at 2.82δ and 3.70δ.

EXAMPLE 4

[1α,2β(Z),3β,4α]-2-[[4-[3-[(Hexyloxy)methyl]-7-oxabicyclo[2.2.1]hept-2-yl]2-butenyl]oxy]-N-hydroxy-N,2,2-trimethylpropanamide A. [1α,2β(Z),3β,4α]-2-[[4-[3-[(Hexyloxy)methyl]-7-oxabicyclo[2.2.1]hept-2-yl]-2-butenyl]oxy]-2-methylacetic acid, t-butyl ester A solution of dry diisopropylamine (0.640 ml; 4.57 mmole) in dry THF (30 ml) was cooled down to −78° under argon and a 1.65M solution of n-BuLi in hexane (2.0 ml; b 1.5 eq.) was added. After 5 minutes, a solution of Example 1 Part D compound (906 mg; 2.28 mmole) in dry THF (10 ml) was added over a period of 2 minutes. After 20 minutes, a solution of dry hexamethyl phosphoric triamide (1.3 ml) in dry THF (1.3 ml) was added, followed by CH3I (0.6 ml). The mixture was stirred at −78° for 3 hours, poured into 10% hydrochloric acid (25 m) and concentrated in vacuo to remove most of the THF. The concentrate was diluted with brine (50 ml) and extracted twice with ether (200 ml) and once with dichloromethane (100 ml). The extracts were washed with a 2.5% sodium thiosulfate solution (40 ml), brine (40 ml), dried (anhydrous MgSO4), filtered and evaporated to afford the crude product as an oil. This was chromatographed on a column of silica gel (Baker, 60–200 mesh, 100 ml), eluting the column with Et2O:hexane (1:9, 1:4) to isolate the homogeneous (TLC) title compound as an oil (840 mg, 89.7%) with a consistent $H^1$-spectrum.

B. [1α,2β(Z), 3β,4α]-2-[[4-[3-[(Hexyloxy)methyl]-7-oxabicyclo[2.2.1]hept-2-yl]-2-butenyl]oxy]-2,2-dimethylacetic acid, t-butyl ester A solution of dry diisopropylamine (0.640 ml; 4.57 mmole) in dry THF (30 ml) was cooled down to −78° under argon and a 1.65M solution of n-BuLi in hexane (2.0 ml; 3.42 mmole) was added. After 5 minutes, a solution of Part A compound (840 mg, 2.05 mmole) in dry THF (10 ml) was added over a period of 2 minutes. After 20 minutes, a solution of dry HMPA (1.3 ml) in dry THF (1.3 ml) was added, followed by CH₃I (0.6 ml, 3.5 eq.). The mixture was stirred at −78° for 3.5 hours, poured into 10% hydrochloric acid (25 ml) and concentrated in vacuo to remove most of the THF. The concentrate was diluted with brine (50 ml) and extracted twice with ether (200 ml) and once with dichloromethane (100 ml). The extracts were washed with a 2.5% sodium thiosulfate solution (40 ml) and brine (40 ml), dried (anhydrous MgSO₄), filtered and evaporated to afford the crude product as an oil. This was chromatographed on a column of silica gel (Baker, 60–200 mesh, 100 ml), eluting the column with Et₂O:hexane (1:9) to isolate the homogeneous TLC) title compound as an oil (713.6 mg, 82%) with consistent H¹ and C¹³-spectral data.

C. [1α,2β(Z),3β,4α]-2-[[4-[3-[(Hexyloxy)methyl]-7-oxabicyclo[2.2.1]hept-2-yl]-2-butenyl]oxy]-2,2-dimethylpropanoic acid A solution of Part B ester (368 mg, 0.87 mmole) and 480 μl (6.17 mmole) of trifluoroacetic acid in dry dichloromethane (25 ml) was refluxed with stirring under nitrogen for 28 hours. The reaction mixture was then cooled to room temperature, diluted with dichloromethane (100 ml) and washed with brine (25 ml). The organic phase was dried (anhydrous MgSO₄), filtered and evaporated to afford the crude product as an oil. This was chromatographed on a silica gel column (Baker, 60–200 mesh, 50 ml) eluting the column with Et₂O:hexane mixtures (1:9; 1:4; 1:1), Et₂O and Et₂O:MeOH (9:1) to isolate the title acid as an oil (268 mg, 83.6%) with consistent analytical, MS, IR, (1740 cm⁻¹, strong, C=O), H¹-NMR and C¹³-NMR data.

Anal calcd for C₂₁H₃₆O₅: C, 68.44; H, 9.85. Found: C, 68.34; H, 9.73.

H¹-NMR spectrum (FX-270, CDCl₃): δ0.88 (t, 3H, J= ~7, H₂₁); 1.18–2.17 (m, 23H, —, —); 3.30–3.47 (m, 4H, —, H₁₄+H₁₆); 3.98 (d, 2H, J= ~6, H₄); 4.38 (d, 1H, J= ~4, H₉); 4.41 (d, 1H, J= ~4, H₁₂); 5.54–5.69 (m, 2H, —, H₅+H₆) ppm.

D. [1α,2β(Z),3β,4α]-2-[[4-[3-[(Hexyloxy)methyl]-7-oxabicyclo[2.2.1]hept-2-yl]-2-butenyl]oxy]-N-hydroxy-N,2,2-trimethylpropanamide A solution of Part C acid (622 mg, 1.68 mmole) and oxalyl chloride (0.4 ml, 4.5 mmole) in dry benzene (10 ml) was cooled down to 0° (ice-water bath), treated with dry dimethylformamide (2 drops) and stirred at 0° for 30 minutes and at room temperature for one hour. The excess oxalyl chloride and solvent were blown off under a stream of nitrogen while heating the flask in a warm water bath and the residual oil was dried in vacuo for one hour. This acid chloride was dissolved in dry tetrahydrofuran (3.3 ml) and added dropwise with stirring into a cold solution (~0°, ice-water) of 98% methylhydroxylamine hydrochloride (294.2 mg, 3.44 mmole) and triethylamine (0.85 ml, 6.91 mmole) in tetrahydrofuran (4.3 ml) and water (4.8 ml). The mixture was stirred at 0° for 30 minutes and at room temperature for 6.5 hours, diluted with water (23 ml) and extracted twice with dichloromethane (110 ml). The combined organic extracts were washed with 1N HCl (23 ml), 5% NaHCO₃ (11 ml) and brine (20 ml), dried (anhydrous MgSO₄), filtered and evaporated to dryness giving an oil (717 mg) containing the desired product and traces of 2 other components.

The mixture was chromatographed on a silica gel column (Baker, 60–200 mesh, 50 ml), eluting the column with mixtures of Et₂O:hexane (1:4, 1:1), Et₂O and Et₂O:MeOH (9:1) to isolate after drying in vacuo the homogeneous (TLC) title compound as an oil (443.4 mg) with consistent elemental analysis, MS, IR (1628 cm⁻¹, strong, C=O), H¹- and C¹³-NMR data. An additional 78.4 mg of impure product was obtained from the column giving a total crude yield of 77.49%. The complexity of both NMR spectra is believed to be due to the presence of several C₁-N rotamers.

H¹-NMR spectrum (FX-270, CDCl₃): δ0.89 (t, 3HH, J= ~7, H₂₁); 1.20–2.16 (m, 22N, —, —); 3.20–3.80 (m, 7H, —, H₁₄+H₁₆+H₂₄); 3.95 (S, broad, 2H, —, H₄); 4.19 (d, 1H, J= ~4, H₉); 4.89 (d, 1H, J= ~4, H₁₂); 5.55 (m, 2H, —, H₅+H₆); 8.57 (s, broad, 1H, —, N—OH) ppm.

EXAMPLE 5

(1α,2β,3β,4α)-2-[[4-[3-[(Hexyloxy)methyl]-7-oxabicyclo[2.2.1]hept-2-yl]butyl]thio]-N-hydroxy-N-methylacetamide A. (1α,2β,3β,4α)-4-[[3-[(Hexyloxy)methyl]-7-oxabicyclo[2.2.1]hept-2-yl]butyl]thioacetate A suspension of 217.3 mg (0.82 mmole) of triphenylphosphine in dry distilled tetrahydrofuran (2.52 ml) was cooled down to 0° under N₂ and treated dropwise with diisopropylazadicarboxylate (0.17 ml; 0.84 mmole). The mixture was then stirred for 30 minutes and treated, dropwise, with a solution of [1α,2β,3β,4α]-4-[3-[(hexyloxy)methyl]-7-oxabicyclo[2.2.1]hept-2-yl]butanol (prepared as described in Example 2 Part A) (117 mg, 0.41 mmole) and thiolacetic acid (0.06 ml) in dry tetrahydrofuran (0.6 ml). The stirring was then continued at 0° for 1 hour and at room temperature for 3 hours. The mixture was then evaporated to dryness on a rotary evaporator and the residue was triturated twice with Et₂O:hexane (1:4, 15 ml), filtering off the white precipitates that formed. The clear filtrate was concentrated to dryness and the resulting syrup was flash chromatographed on a silica gel column (LPS-1) eluting the column with Et₂O:hexane (1:9, 1.0 liter). The desired fractions were combined to give 128.8 mg (91.7%) of the title thioacetate as a homogeneous (TLC) oil with consistent H¹ and C¹³-NMR spectral data.

B. (1α,2β,3β,4α)-4-[3-[(Hexyloxy)methyl]-7-oxabicyclo[2.2.1]hept-2-yl]butanethiol A suspension of lithium aluminum hydride (17.1 mg, 0.45 mmole) in dry distilled tetrahydrofuran (1 ml) was cooled down to 0° under N₂ and treated with a solution of 128.8 mg (0.367 mmole) of the Part A thioacetate in dry tetrahydrofuran. The mixture was stirred at 0° for 1 hour then quenched by the successive addition of water (0.02 ml), 10% Na₂SO₄ (0.05 ml) and water (0.06 ml). The mixture was stirred for 30 minutes, diluted with dichloromethane (10 ml) and filtered, washing the salts well with dichloromethane (20 ml). The filtrate was dried (anhydrous MgSO₄), filtered and concentrated to give 113 mg (100%) of title thiol compound as an oil (homogeneous by TLC) with consistent H¹ and C¹³-NMR spectra.

C. (1α,2β,3β,4α)-2-[[4-[3-[(Hexyloxy)methyl]-7-oxabicyclo[2.2.1]hept-2-yl]butyl]thio]acetic acid, methyl ester A solution of 340 mg (1.13 mmole) of the Part B thiol in dry acetone (12 ml) was treated with 609 mg (4.41 mmole) of potassium carbonate (anhydrous) and methyl bromoacetate (0.21 ml, 2.20 mmole) and stirred at room temperature for 3 hours. The mixture was then diluted with ether (30 ml), dried (anhydrous MgSO4) and filtered, washing the precipitates well with ether (120 ml). The filtrate and washings were combined and evaporated to give 449 mg of title ester compound as an oil which had trace amounts of two other by-products (TLC). This crude mixture was flash-chromatographed on a silica gel column (LPS-1) using Et2O:hexane (1:9, 6.0 liters). The fractions containing the desired product were combined and concentrated to give 367 mg (87.2%) of title ester compound as a homogeneous oil (TLC) with consistent $H^1$ and $C^{13}$-NMR data.

D. (1α,2β,3β,4α)-2-[[4-[3-[(Hexyloxy)methyl]-7-oxabicyclo[2.2.1]hept-2-yl]butyl]thio]acetic acid A stirred solution of 367.3 mg (0.99 mmole) of Part C ester in tetrahydrofuran (70.7 ml) and water (17.3 ml) was cooled down to 0° C. and argon was bubbled in for 30 minutes. Hydroquinone (10 mg) was then added to the solution followed by 1N LiOH (10 ml) and the bubbling of argon was continued. After 30 minutes at 0° and 4 hours at room temperature the mixture was acidified with 1N HCl (10 ml). After 30 minutes the organic solvent was evaporated in vacuo and the aqueous suspension was diluted with water (25 ml) and extracted twice with dichloromethane (130 ml). The organic phase was dried (anhydrous MgSO4), filtered and concentrated to give 311 mg of a yellow oil containing the desired product and a small amount of another component at the solvent front. This oil was chromatographed 3 times on a silica gel column (Baker) in order to get rid of the contaminant and hydroquinone, eluting the columns with decreasing concentrations of hexane in ethyl acetate:hexane solutions (50% to 10%). The desired fractions were combined, evaporated and dried in vacuo to give 144 mg (40.6%) of the title acid as a homogeneous (tlc) light yellow oil with consistent IR, MS, $H^1$-NMR and $C^{13}$-NMR spectral data.

Anal Calcd for $C_{19}H_{34}O_4S$: C, 63.65; H, 9.56; S, 8.94. Found: C, 63.58; H, 9.54; S, 8.78.

$^1$H-NMr (270 MHz, CDCl3): δ0.89 (t, 3H, J=~7.0, H21); 1.2-1.8 (m, 20H, —, —); 2.04 (q, 1H, J=~4.0, H13); 2.65 (t, 2H, J=~7, H4); 3.23 (s, 2H, —, H2); 3.2-3.5 (m, 4H, —, H14 & H16); 4.26 (d, 1H, J=~4, H9); 4.43 (d, 1H, J=~4, H10) ppm.

E. (1α,2β,3β,4α)-2-[[4-[3-[(Hexyloxy)methyl]-7-oxabicyclo[2.2.1]hept-2-yl]butyl]thio]-N-hydroxy-N-methylacetamide Following the procedure of Example 1 Part F except substituting the above Part D acid for the Example 1 Part E acid, the title compound is obtained.

EXAMPLE 6

(1α,2β,3β,4α)-2-[[4-[3-[(Hexylthio)methyl]-7-oxabicyclo[2.2.1]hept-2-yl]butyl]oxy]-N-hydroxy-N-methylacetamide A. (1α,2β,3β,4α)-Cis-exo-7-oxabicyclo[2.2.1]heptane-2,3-dimethanol To a suspension of 11.4 g lithium aluminum hydride (300 mmole, 1.6 eq.) in 400 ml of dry THF at 0° C. was added dropwise a solution of 32 g cis-exo-7-oxabicyclo[2.2.1]heptane-2,3-dicarboxylic anhydride (190 mmole) in 400 ml of dry THF over a period of 1 hour. The reaction mixture was stirred at 25° C. for 18 hours, cooled to 0° C. and quenched by slow addition of a saturated Na2SO4 solution, and filtered. The solid was washed with three 100 ml portions of CH2Cl2. The combined organic layer was dried over MgSO4 and concentrated to give 32 g of title diol as a colorless acid.

A'. (1α,2β,3β,4α)-Cis-exo-2-hydroxymethyl-3-[(phenylmethoxy)methyl]-7-oxabicyclo[2.2.1]heptane To a suspension of 3.08 g of sodium hydride (70 mmole, 50% oil dispersion), washed with ether, in 100 ml of dry DMF was added with stirring at 0° C. a solution of 10.0 g title A diol (64 mmole) in 30 ml of DMF over a period of 15 minutes. The mixture was stirred for 30 minutes at 0° C., 20 minutes at 25° C., recooled to 0° C. and 12.0 g of benzyl bromide (70 mmole) was added dropwise. After stirring at 25° C. for 2 hours, the reaction was quenched with an aqueous ammonium chloride solution, extracted with ether, dried over anhydrous MgSO4 and concentrated.

Purification was done on a silica gel column, eluting with 10-20% ethyl acetate in hexane to give 11.8 g of the title monobenzylether.

B. (1α,2β,3β,4α)-2-Chloromethyl-3-[(Phenylmethoxy)methyl]-7-oxabicyclo[2.2.1]heptane A solution of the Part A' compound (20 mmole), p-toluene sulfonyl chloride (21 mmole) and pyridine (4.0 ml) is stirred in dichloromethane (20 ml) for 20 hours at room temperature. The mixture is then diluted with ether (100 ml), washed with cold 10% hydrochloric acid (2×10 ml), a 10% Na2CO3 solution and water, dried (MgSO4 anhydrous), evaporated and the residual oil is subjected to flash chromatography on LPS-1 silica gel to afford the title compound.

C. (1α,2β,3β,4α)-2-(Cyanomethyl)-3-[(Phenylmethoxy)methyl]-7-oxabicyclo[2.2.1]heptane A solution of Part B compound (13 mmole) and sodium cyanide (1.5 g) in dry dimethylsulfoxide (15 ml) is heated in a bath at 90°-95° for 18 hours. The mixture is then cooled to room temperature, diluted with water (75 ml) and is extracted with ether (3×40 ml). The ether extracts are combined, washed with water (2×10 ml), dried (MgSO4 anhydrous) and the residual oil is flash chromatographed on a silica gel (LPS-1) column to isolate the title compound.

D. (1α,2β,3β,4α)-2-(Formylmethyl)-3-[(Phenylmethoxy)methyl]-7-oxabicyclo[2.2.1]heptane A solution of Part C compound (10 mmole) in dry toluene (20 ml) is stirred under argon in a bath at −78° and a 1.5 molar solution of diisobutyl aluminum hydride (10 ml) is added. After 4 hours, the mixture is quenched by the addition of 10% hydrochloric acid (30 ml), warmed to room temperature and is extracted with ether (3×30 ml). The extracts are combined, washed with 10% hydrochloric acid and dilute brine, dried (MgSO4 anhydrous) and is evaporated to afford the title compound as an oil.

E. (1α,2β,3β,4α)-4-[[3-(Phenylmethoxy)methyl]-7-oxabicyclo[2.2.1]hept-2-yl]-2-butenoic acid, methyl ester

[Wadsworth-Emmons reaction—W. C. Still, C. Gennari,, Tetrahedron Letters, 26, No. 41, 4405 (1983)]

A suspension of 50% sodium hydride in paraffin (8.75 mmole, 420 mg) in dry THF (60 ml) is cooled and stirred in an ice-bath under an atmosphere of argon and trimethylphosphonoacetate (12.4 mmole, 2.4 ml) is added. The resulting slurry is stirred for 30 minutes at room temperature for 1 hour. It is then recooled in the ice-bath and a solution of the Part D aldehyde (7.9 mmole) in dry THF (20 ml) is added. After stirring for 30 minutes in the ice-bath and at ambient temperature for 2 hours, glacial acetic acid (2.0 ml) is added and the mixture is evaporated to dryness in vacuo. After dilution of the residue with water (100 ml), the product is extracted into ether (3×50 ml). The extracts were combined, washed with water, dried (MgSO₄ anhydrous), filtered, evaporated and the residue is chromatographed on a column of silica gel to isolate the title compound.

F. (1α,2β,3β,4α)-4-[[3-(Phenylmethoxy)methyl]-7-oxabicyclo[2.2.1]hept-2-yl]-2-butenol A solution of Part E compound (10 mmole) in dry toluene is reduced using 1.5 molar diisobutyl aluminum hydride in toluene (20 ml) as in Example 1 Part C to afford the title compound as an oil.

G. (1α,2β,3β,4α)-2-[[[4-[3-(Phenylmethoxy)methyl]-7-oxabicyclo[2.2.1]hept-2-yl]-2-butenyl]oxy]acetic acid, 1,1-(dimethyl)ethyl ester A mixture of Part F compound (3.0 mmole), t-butylbromoacetate (5.0 ml), tetrabutyl ammonium sulfate (1.7 g), tetrahydrofuran (20 ml) and 50% sodium hydroxide (20 ml) is vigorously stirred under argon for 2½ hours. Most of the tetrahydrofuran is removed by concentration in vacuo and the residue is extracted with dichloromethane (3×30 ml). The extracts are combined, washed with water, dried (MgSO₄ anhydrous), evaporated and the residue is flash chromatographed on LPS-1 silica gel to afford the title compound.

H. (1α,2β,3β,4α)-2-[[4-[3-(Hydroxymethyl)-7-oxabicyclo[2.2.1]hept-2-yl]-2-butyl]oxy]acetic acid, 1,1-(dimethyl)ethyl ester A solution of Part G compound (5.0 mmole) in methanol (25 ml) containing 5% palladium on carbon (50 mg) is stirred under an atmosphere of hydrogen for 2 hours. It is then filtered through a bed of celite and is evaporated to afford the title compound.

I. (1α,2β,3β,4α)-2-[[4-[3-[(Acetylthio)methyl]-7-oxabicyclo[2.2.1]hept-2-yl]-2-butyl[oxy]acetic acid, 1,1-dimethyl(ethyl) ester Triphenyl phosphine (8 mmole) is stirred in dry THF (30 ml) in an ice-bath under an atmosphere of argon and diisopropylazadicarboxylate (8.0 mmole) is added. After 15 minutes, a solution of Part H compound (8.0 mmole) in dry THF (10 ml) is added followed by thiolacetic acid (8.1 mmole) in dry THF (5.0 ml). After stirring for ½ hour in the ice-bath and 4 hours at room temperature, the mixture is concentrated in vacuo and the residual syrup is flash chromtographed to isolate the title compound.

J. (1α,2β,3β,4α)-2-[[4-[3-[(Hexylthio)methyl]-7-oxabicyclo[2.2.1]hept-2-yl]-2-butyl]oxy]acetic acid, 1,1-(dimethyl)ethyl ester A solution of Part I compound (5.0 mmole) in dry methanol (20 ml) containing anhydrous K₂CO₃ (10 mmole) and n-hexyl bromide (12 mmole) is stirred in an ice-bath under an atmosphere of argon for 4 hours. The mixture is then concentrated in vacuo, diluted with water and is extracted with ether. The ether extract is dried (MgSO₄ anhydrous), evaporated and the residue is flash chromatographed on silica gel (LPS-1) to isolate the title compound.

K. (1α,2β,3β,4α)-2-[[4-[3-[(Hexylthio)methyl]-7-oxabicyclo[2.2.1]hept-2-yl]-2-butyl]oxy], acetic acid A solution of Part J compound (5.0 mmole) in dry dichloromethane (20 ml) is stirred at room temperature with a solution of trifluoroacetic acid (10 mmole) in dichloromethane (5.0 ml) for 4 hours. The solution is then washed with dilute brine (3×10 ml), dried (MgSO₄ anhydrous) and is evaporated to afford the title compound.

L. (1α,2β,3β,4α)-2-[[4-[3-[(Hexylthio)methyl]-7-oxabicyclo[2.2.1]hept-2-yl]butyl]oxy]-N-hydroxy-N-methylacetamide Following the procedure of Example 1 Part F except substituting the Example 8 Part K acid for the Example 1 Part E acid, the title compound is obtained.

EXAMPLE 7

(1α,2β,3β,4α)-2-[[4-[3-[(Hexylthio)methyl]-7-oxabicyclo[2.2.1]hept-2-yl]butyl]thio]-N-hydroxy-N-methylacetamide A. (1α,2β,3β,4α)-4-[[3-(Hydroxymethyl)-7-oxabicyclo[2.2.1]hept-2-yl]butanol A solution of Example 6 Part F compound (5.0 mmole) in methanol (25 ml) containing 5% Pd/c (50 mg) is stirred under an atmosphere of hydrogen for 4 hours. Filtration of the mixture through a bed of celite followed by evaporation gives the title compound.

B. (1α,2β,3β,4α)-2-[4-(Acetylthio)butyl]-7-oxabicyclo[2.2.1]heptane-3-methanol

A solution of Part A compound in dry THF is reacted as described in Example 6 Part I and the product is isolated to afford the title compound.

C. (1α,2β,3β,4α)-4-[3-(Hydroxymethyl)-7-oxabicyclo[2.2.1]hept-2-yl]butanethiol

To a cooled (ice-bath) and stirred suspension of lithium aluminum hydride (10 mmole) in dry tetrahydrofuran (20 ml) is added a solution of the Part B compound (3.0 mmole) in dry THF (50 ml) in the course of 3 minutes. The mixture is stirred for 1 hour, and is carefully decomposed by the addition of a 20% sodium sulfate solution. The mixture is then filtered through a bed of celite and the celite is washed with small amounts of dry tetrahydrofuran. The filtrate and washings are combined, dried (MgSO₄ anhydrous) and the resulting mixture is evaporated to afford the title compound as an oil.

D. (1α,2β,3β,4α)-2-[[4-[3-(Hydroxymethyl)-7-oxabicyclo[2.2.1]hept-2-yl]butyl]thio]acetic acid, methyl ester A solution of Part C compound (5 mmole), powdered K₂CO₃ (20 mmole) and methylbromoacetate (10 mmole) is stirred in dry methanol (30 ml) for 3 hours under an atmosphere of nitrogen. The mixture is then concentrated in vacuo, diluted with ether (50 ml), washed with water, dried (MgSO₄ anhydrous) and is evaporated to afford an oil. This is flash chromatographed on a column of silica gel (LPS-1) to isolate the title compound.

E.  (1α,2β,3β,4α)-2-[[[4-[3-(Acetylthio)methyl]-7-oxabicyclo[2.2.1]hept-2-yl]butyl]thio]acetic acid, methyl ester Part D compound is reacted with thioacetic acid by the procedure described in Example 6 Part I and is processed to afford the title compound.

F.  (1α,2β,3β,4α)-2-[[4-[3-[(Hexylthio)methyl]-7-oxabicyclo[2.2.1]hept-2-yl]butyl]thio]acetic acid, methyl ester A solution of Part E compound (5.0 mmole) in dry methanol (25 ml) containing anhydrous $K_2CO_3$ is stirred at room temperature in an ice bath under an atmosphere of argon for 2 hours. Then, n-hexyl bromide (7 mmole) is added and the stirring is continued for 5 hours. The mixture is then concentrated in vacuo, diluted with water and is extracted with ether. The ether extracts are combined, dried ($MgSO_4$ anhydrous), evaporated and the residue is chromatographed on a column of silica gel to isolate the title compound.

G.  (1α,2β,3β,4α)-2-[[4-[3-[(Hexylthio)methyl]7-oxabicyclo[2.2.1]hept-2-yl]butyl]thio]acetic acid A carefully degassed solution of Part F compound (3.0 mmole) in tetrahydrofuran (15 ml) containing 2N lithium hydroxide (10 ml) is refluxed under an atmosphere of argon for 5 hours. The mixture is then cooled to room temperature and is acidified with 10% hydrochloric acid. It is then concentrated in vacuo, diluted with water and is extracted with ether. The ether extracts are combined, washed with water, dried ($MgSO_4$ anhydrous) and the mixture is evaporated to afford the title compound.

H.  (1α,2β,3β,4α)-2-[[4-[3-[(Hexylthio)methyl]-7-oxabicyclo[2.2.1]hept-2-yl]butyl]thio]-N-hydroxy-N-methylacetamide Following the procedure of Example 1 Part F except substituting the Part G acid for the Example 1 Part C acid, the title compound is obtained.

EXAMPLE 8

[1α,2β(Z),3β,4α]-2-[[4-[3-[(Hexyloxy)methyl]-7-oxabicyclo[2.2.1]hept-2-yl]-2-butenyl]thio]acetic acid A.  [1α,2β(Z),3β,4α]-4-[3-[(Hexyloxy)methyl]-7-oxabicyclo[2.2.1]hept-2-yl]-2-butene thiol, acetic acid ester To a cooled (ice bath) and stirred suspension of triphenylphosphine (6.0 mmole) in dry THF (20 ml) is added diisopropylazadicarboxylate (6.0 mmole). After 30 minutes a solution of [1α,2β(Z),3β,4α]-4-[3-[(hexyloxy)methyl]-7-oxabicyclo[2.2.1]hept-2-yl]-2-butenol (3.0 mmole) and thiol acetic acid (6.0 mmole) in dry THF (5.0 ml) is added. The mixture is then stirred in the ice-bath for 1 hour and at room temperature for 3 hours. It is then concentrated in vacuo and the residue is triturated twice with ether-hexane (1:3, 30 ml each), removing the solids by filtration. The filtrate is evaporated and the residue is flash chromatographed on a silica gel (LPS-1) column eluting with ether-hexane (1:9) to isolate the title compound.

B.  [1α,2β(Z),3β,4α]-4-[3-[(Hexyloxy)methyl]-7-oxabicyclo[2.2.1]hept-2-yl]-2-butene thiol To a cooled (ice bath) and stirred suspension of lithium aluminum hydride (2.0 mmole) in dry THF (10 ml) is added a solution of Part A ester compound (2.0 mmole) in dry THF. After 1 hour, a mixture of water (0.5 ml) and THF (2.0 ml) is added dropwise. After stirring for 30 minutes, the mixture is filtered through a bed of celite, washing the celite with small amounts of THF. The filtrate and washings are combined, dried ($MgSO_4$ anhydrous), filtered and is evaporated to afford the title compound as an oil.

C.  [1α,2β(Z),3β,4α]-2-[[4-[3-[(Hexyloxy)methyl]-7-oxabicyclo[2.2.1]hept-2-yl]-2-butenyl]thio]acetic acid, methyl ester A solution of Part B thiol compound (1.5 mmole) in dry acetone (15 ml) is stirred under an atmosphere of nitrogen with anhydrous $K_2CO_3$ (4.0 mmole) and methyl bromo acetate (3.0 mmole) at ambient temperature for 3 hours. The mixture is then diluted with ether (60 ml) and is filtered. The filtrate is evaporated in vacuo and is flash chromatographed on a column of silica gel (LPS-1) using $Et_2O$-hexane (1:9) for elution to isolate the title compound.

D.  [1α,2β(Z),3β,4α]-2-[[4-[3-[(Hexyloxy)methyl]-7-oxabicyclo[2.2.1]hept-2-yl]-2-butenyl]thio]acetic acid A mixture of THF (30 ml), water (8.0 ml) and 2N LiOH (5.0 ml) is stirred in an ice bath and argon gas is bubbled in for 30 minutes. A solution of Part C ester compound (1.0 mmole) and hydroquinone (15 mg) in THF (2.0 ml) is then added and the bubbling of argon is continued. After stirring in the ice bath for 30 minutes and at ambient temperature for 4 hours, the mixture is acidified with 1N HCl (11 ml) and is concentrated in vacuo. The concentrate is diluted with water (30 ml) and is extracted with $CH_2Cl_2$ (2×30 ml). The extracts are combined, washed with water, dried ($MgSO_4$ anhydrous), filtered and is evaporated to afford the crude product. This is purified by chromatography on silica gel (Baker 60–200 mesh) eluting the column with ether hexane mixtures to isolate the title compound.

EXAMPLE 9

[1α,2β(Z),3β,4α]-2-[[4-[3-[(Hexylthio)methyl]-7-oxabicyclo[2.2.1]hept-2-yl]-2-butenyl]thio]acetic acid A.  [1α,2β(Z),3β,4α]-4-[3-[(Hydroxy)methyl]-7-oxabicyclo[2.2.1]hept-2-yl]-2-butenoic acid, methyl ester A solution of (exo)-octahydro 5,8-epoxy-1H-benzopyran-3-ol (3.9) mmole and carboxymethyl triphenyl phosphorane (3.9 mmole) in dry THF (20 ml) is stirred at room temperature. After 20 hours, a 25% $NH_4Cl$ solution (40 ml) is added and the mixture is concentrated in vacuo to remove most of the THF. The concentrate is extracted with ether (3×70 ml). The extracts are combined, washed with water (2×20 ml), dried ($MgSO_4$ anhydrous), filtered and is evaporated to an oil. This is subjected to a flash chromatography on silica gel (LPS-1) eluting the column with ethyl acetate-hexane (3:7) to isolate the title compound.

B.  [1α,2β(Z),3β,4α]-2-[4-[3-[(Acetyl)thio]methyl]-7-oxabicyclo[2.2.1]hept-2-yl]-2-butenoic acid, methyl ester To a cooled (ice bath) and stirred suspension of triphenylphosphine (8.0 mmole) in dry THF (30 ml) is added diisopropylazadicarboxylate (8.0 mmole). After 30 minutes, a solution of Part A alcohol compound (6.0 mmole) and thiol acetic acid (6.0 mmole) in dry THF (5.0 ml) is added. The mixture is then stirred in the ice bath for 30 minutes and at room temperature for 8 hours. It is then concentrated in vacuo and the residue is triturated twice with ether-hexane (1:3, 30 ml each) removing the insoluble solids by decantation. The solvent is then evaporated and the residue is flash chromatographed on a column of silica gel (LPS-1) eluting the column with ether-hexane (15:85) to isolate the title compound.

C. [1α,2β(Z),3β,4α]-2-[4-[3-[(Hexylthio)methyl]-7-oxabicyclo[2.2.1]hept-2-yl]-2-butenoic acid, methyl ester A solution of Part B thiolacetate (4.0 mmole), anhydrous $K_2CO_3$ (12 mmole), and n-hexyl bromide (6.0 mmole) in argon-purged methanol (20 ml) is stirred under an atmosphere of argon for 18 hours. The mixture is then acidified with 1N HCl (12 ml) and is concentrated in vacuo. The concentrate is diluted with brine (25 ml) and is extracted with ether (3×20 ml). The extracts are combined, washed with water, dried ($MgSO_4$ anhydrous) and is evaporated to afford an oil. This is purified by flash chromatography on a silica gel column (LPS-1) eluting with ether-hexane (15:85) to isolate the title compound.

D. [1α,2β(Z),3β,4α]-4-[3-[(Hexylthio)methyl]-7-oxabicyclo[2.2.1]hept-2-yl]-2-butenol A solution of Part C thioether compound (4.0 mmole) in dry toluene (35 ml) is stirred in a bath at −78° under argon and a 1.5M solution of diisobutyl aluminum hydride in toluene (8.0 ml) is added. After 4 hours, the mixture is added under stirring into 10% hydrochloric acid (30 ml) and is extracted with ether (3×40 ml). The extracts are combined, washed with water, dried ($MgSO_4$ anhydrous) and is evaporated to afford the title compound.

E. [1α,2β(Z),3β,4α]-4-[3-[(Hexylthio)methyl]-7-oxabicyclo[2.2.1]hept-2-yl]-2-butenethiol, acetic acid ester A solution of Part D thioether compound (3.0 mmole) is reacted under the conditions described above for the conversion of compound A into compound B to isolate the title compound.

F. [1α,2β(Z),3β,4α]-2-[[4-[3-[(Hexylthio)methyl]-7-oxabicyclo[2.2.1]hept-2-yl]-2-butenyl]thio]acetic acid, 2,2-(dimethyl)ethyl ester A solution of Part E thioether compound (2.5 mmole) in argon-purged methanol (20 ml) containing anhydrous $K_2CO_3$ (7.5 mmole) and t-butylbromoacetate (5.0 mmole) is stirred under an atmosphere of argon for 6 hours. The mixture is then acidified with 1N HCl (8 ml) and is concentrated in vacuo. The concentrate is diluted with brine (20 ml) and is extracted with ether (3×20 ml). The extracts are combined, washed with water, dried ($MgSO_4$ anhydrous) and is evaporated to afford an oil. This is purified by flash chromatography on a column of silica gel (LPS-1) eluting with ethyl acetate hexane (1:9) to isolate the title compound.

G. [1α,2β(Z),3β,4α]-2-[[4-[3-[(Hexylthio)methyl]-7-oxabicyclo[2.2.1]hept-2-yl]-2-butenyl]thio]acetic acid A solution of Part F thioether compound (1.0 mmole) in dry $CH_2Cl_2$ (10 ml) is stirred in an ice bath and trifluoroacetic acid (0.2 ml) and anisole (0.1 ml) is added. After 2 hours, the mixture is diluted with $CH_2Cl_2$ (10 ml), washed with water (3×10 ml), dried ($MgSO_4$ anhydrous) and is evaporated to afford an oil. This is purified by chromatography on a column of silica gel (Baker 60-200 mesh) eluting with ether-hexane mixtures to isolate the title compound.

EXAMPLE 10

(1α,2β,3β,4α)-2-[[4-[3-[2-(Hexylthio)ethyl]-7-oxabicyclo[2.2.1]hept-2-yl]butyl]oxy]-N-hydroxy-N-methylacetamide A. [1α,2β(Z),3β,4α]-7-[[[3-(2-Oxo)ethyl-7-oxabicyclo[2.2.1]hept-2-yl]-butyl]oxy]acetic acid, methyl ester Into a dry 100 ml round bottom 3-necked flask containing a stir bar was added dried 12.9 g (37.7 mmoles) methoxymethyltriphenylphosphonium chloride (($C_6H_5$)$_3$P$^+$—$CH_2OCH_3Cl^-$) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) (1α,2β,3β,4α)-2-[[4-[3-(formyl)-7-oxabicyclo[2.2.1]hept-2-yl]butyl]oxy]acetic acid, methyl ester in 60 ml toluene was added by means of a dropping funnel over a 35 minute period with the ice-bath still in place. After 5 hours, the reaction was quenched by addition of 2.3 g (39 mmol) acetic acid in 5 ml ether. The reaction mixture immediately turned pale yellow and was immediately poured into 200 ml saturated $NH_4Cl$, and extracted with ether (4×200 ml). The combined ether phases were washed with a saturated NaCl solution, dried ($MgSO_4$) and concentrated to yield a yellow oil in a white crystalline solid (phosphine oxide). The white solid removed after trituration with EtOAc and the mother liquors was treated with trifluoroacetic acid and was purified by chromatography to afford the title compound.

B. (1α,2β,3β,4α)-2-[[4-[3-(2-Hydroxyethyl)-7-oxabicyclo[2.2.1]hept-2-yl]butyl]oxy]acetic acid, methyl ester The aldehyde (1.4 g, 5 mmol) from part A in methanol (50 ml) is treated with $NaBH_4$ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated $KHCO_3$, saturated NaCl and dried ($MgSO_4$ anhydrous). The ether is evaporated to yield the title B compound.

C. (1α,2β,3β,4α)-2-[[4-[3-[2-(Hexylthio)ethyl]-7-oxabicyclo[2.2.1]hept-2-yl]butyl]oxy]-N-hydroxy-N-methylacetamide Following the procedure of Example 6 except substituting the above part B alcohol for the alcohol used in Example 6 Part I, the title compound is obtained.

EXAMPLE 11

(1α,2β,3β,4α)-2-[[4-[3-[4-(Hexylthio)butyl]-7-oxabicyclo[2.2.1]hept-2-yl]butyl]oxy]-N-hydroxy-N-methylacetamide A. (1α,2β,3β,4α)-[[4-[3-(3-Oxo)propyl-7-oxabicyclo[2.2.1]hept-2-yl]butyl]oxy]acetic acid, methyl ester Following the procedure of Example 10 Part A except substituting (1α,2β(Z),3β,4α)-7-[3-(2-oxo)ethyl-7-oxabicyclo[2.2.1]hept-2-yl]-5-heptenoic acid, methyl ester for [1α,2β(Z),3β,4α]-7-[3-formyl-7-oxabicyclo[2.2.1]hept-2-yl]-5-heptenoic acid, methyl ester, the title A compound is obtained.

B. (1α,2β,3β,4α)-2-[[4-[3-(4-Oxo)butyl-7-oxabicyclo[2.2.1]hept-2-yl]butyl]oxy]acetic acid, methyl ester Following the procedure of Example 10 Part A except substituting the aldehyde from Part A above for (1α,2β,3β,4α)-2-[[[4-[(formyl)-7-oxabicyclo[2.2.1]hept-2-yl]butyl]oxy]acetic acid, methyl ester, the title B compound is obtained.

C. (1α,2β,3β,4α)-2-[[4-[3-(4-Hydroxybutyl)-7-oxabicyclo[2.2.1]hept-2-yl]butyl]oxy]acetic acid, methyl ester Following the procedure of Example 10 Part B except substituting the title B aldehyde for (1α,2β,3β,4α)-2-[[4-[3-(2-oxo)ethyl-7-oxabicyclo[2.2.1]hept-2-yl]butyl]oxy]acetic acid, methyl ester, the title C alcohol is obtained.

D. (1α,2β,3β,4α)-2-[[4-[3-[4-(Hexylthio)butyl]-7-oxabicyclo[2.2.1]hept-2-yl]butyl]oxy]-N-hydroxy-N-methylacetamide Following the procedure of Example 6 except substituting the above Part C alcohol for the alcohol used in Example 1 Part I, the title compound is obtained.

EXAMPLES 12 TO 55

Following the procedures outlined above and set out in the working Examples, the following additional compounds, in accordance with the following invention, may be prepared.

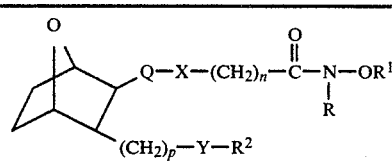

| Ex. No. | Q | X | $(CH_2)_n$ | R | $R^1$ | p | Y | $R^2$ |
|---|---|---|---|---|---|---|---|---|
| 12. | $-CH_2-CH=CH-(CH_2)_2-$ | O | $(CH_2)_2$ | $C_3H_7$ | $CH_3$ | 1 | O | $C_6H_5$ |
| 13. | $-CH_2-CH=CH-$ | O | $-CH_2CH-$ with $CH_3$ branch | $C_2H_5$ | H | 2 | O | $C_6H_5CH_2$ |
| 14. | $-CH_2-CH=CH-(CH_2)_3-$ | O | $-(CH_2)_3-$ | H | $C_2H_5$ | 2 | O | cyclohexyl |
| 15. | $-CH_2-CH=CH-(CH_2)_4-$ | O | $-(CH_2)_4-$ | $CH_3$ | $C_6H_5$ | 1 | O | cyclopentyl-$CH_2-$ |
| 16. | $-CH_2CH=CH-CH_2-$ | O | $-(CH_2)_2-$ | $CH_3$ | $CH_3$ | 3 | O | $CH_3CH_2CH=CH-CH_2-$ |
| 17. | $-CH_2-CH=CH-$ | O | $-(CH_2)_3$ | H | H | 3 | O | $CH_3CH_2\equiv C-CH_2-$ |
| 18. | $-CH_2-(CH_2)_2-CH_2-$ | O | $(CH_2)_2-$ | $CH_3$ | $C_6H_5CH_2$ | 1 | O | $C_3H_7$ |
| 19. | $-CH_2-(CH_2)_2-$ | O | $-(CH_2)_3-$ | $C_6H_{13}$ | cyclohexyl | 2 | O | $C_6H_5$ |
| 20. | $-CH_2-(CH_2)_2-(CH_2)_2-$ | O | $-(CH_2)_4-$ | H | cyclopentyl-$CH_2$ | 4 | O | $C_6H_5-(CH_2)_2-$ |
| 21. | $-CH_2-(CH_2)_2-(CH_2)_4-$ | O | $-(CH_2)_3$ | $C_2H_5$ | $CH_3\overset{O}{\underset{\|}{C}}-$ | 2 | O | cyclohexyl |

-continued

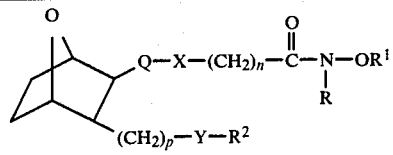

| Ex. No. | Q | X | (CH$_2$)$_n$ | R | R$^1$ | p | Y | R$^2$ |
|---|---|---|---|---|---|---|---|---|
| 22. | —CH$_2$—(CH$_2$)$_3$—(CH$_2$)$_3$— | O | —(CH$_2$)$_2$— | C$_3$H$_7$ | C$_6$H$_5$—C(=O)— | 3 | O | cyclohexyl-CH$_2$— |
| 23. | —CH$_2$—CH=CH—(CH$_2$)$_2$— | S | (CH$_2$)$_2$ | (CH$_3$)$_3$C | CH$_3$ | 1 | O | C$_6$H$_5$ |
| 24. | —CH$_2$—CH=CH— | S | —CH$_2$CH(CH$_3$)— | C$_4$H$_9$ | H | 2 | O | C$_6$H$_5$CH$_2$ |
| 25. | —CH$_2$—CH=CH—(CH$_2$)$_3$— | S | —(CH$_2$)$_3$— | H | C$_2$H$_5$ | 2 | O | cyclohexyl |
| 26. | —CH$_2$—CH=CH—(CH$_2$)$_4$— | S | —(CH$_2$)$_4$— | CH$_3$ | C$_6$H$_5$ | 1 | O | cyclopentyl-CH$_2$— |
| 27. | —CH$_2$CH=CH—CH$_2$— | S | —(CH$_2$)$_2$— | CH$_3$ | CH$_3$ | 3 | O | CH$_3$CH$_2$CH=CH—CH$_2$— |
| 28. | —CH$_2$—CH=CH— | S | —(CH$_2$)$_3$ | H | H | 3 | O | CH$_3$CH$_2$≡C—CH$_2$— |
| 29. | —CH$_2$—(CH$_2$)$_2$—CH$_2$— | S | (CH$_2$)$_2$— | CH$_3$ | C$_6$H$_5$CH$_2$ | 1 | O | C$_3$H$_7$ |
| 30. | —CH$_2$—(CH$_2$)$_2$— | S | —(CH$_2$)$_3$— | CH$_3$ | cyclohexyl | 2 | O | C$_6$H$_5$ |
| 31. | —CH$_2$—(CH$_2$)$_2$—(CH$_2$)$_2$— | S | —(CH$_2$)$_4$— | H | cyclopentyl-CH$_2$ | 4 | O | C$_6$H$_5$—(CH$_2$)$_2$— |
| 32. | —CH$_2$—(CH$_2$)$_2$—(CH$_2$)$_4$— | S | —(CH$_2$)$_3$ | C$_2$H$_5$ | CH$_3$C(=O)— | 2 | O | cyclopentyl |
| 33. | —CH$_2$—(CH$_2$)$_3$—(CH$_2$)$_3$— | S | —(CH$_2$)$_2$— | C$_3$H$_7$ | C$_6$H$_5$—C(=O)— | 3 | O | cyclohexyl-CH$_2$— |
| 34. | —CH$_2$—CH=CH—(CH$_2$)$_2$— | O | (CH$_2$)$_2$ | CH$_3$ | CH$_3$ | 1 | S | C$_6$H$_5$ |
| 35. | —CH$_2$—CH=CH— | O | —CH$_2$CH(CH$_3$)— | C$_2$H$_5$ | H | 2 | S | C$_6$H$_5$CH$_2$ |
| 36. | —CH$_2$—CH=CH—(CH$_2$)$_3$— | O | —(CH$_2$)$_3$— | H | C$_2$H$_5$ | 2 | S | cyclohexyl |
| 37. | —CH$_2$—CH=CH—(CH$_2$)$_4$— | O | —(CH$_2$)$_4$— | CH$_3$ | C$_6$H$_5$ | 1 | S | cyclopentyl-CH$_2$— |
| 38. | —CH$_2$CH=CH—CH$_2$— | O | —(CH$_2$)$_2$— | CH$_3$ | CH$_3$ | 3 | S | CH$_3$CH$_2$CH=CH—CH$_2$— |
| 39. | —CH$_2$—CH=CH— | O | —(CH$_2$)$_3$ | H | H | 3 | S | CH$_3$CH$_2$≡C—CH$_2$— |
| 40. | —CH$_2$—(CH$_2$)$_2$—CH$_2$— | O | (CH$_2$)$_2$ | CH$_3$ | C$_6$H$_5$CH$_2$ | 1 | S | C$_3$H$_7$ |

-continued

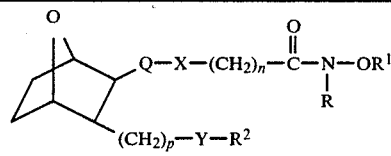

| Ex. No. | Q | X | $(CH_2)_n$ | R | $R^1$ | p | Y | $R^2$ |
|---|---|---|---|---|---|---|---|---|
| 41. | $-CH_2-(CH_2)_2-$ | O | $-(CH_2)_3-$ | $CH_3$ | cyclohexyl | 2 | S | $C_6H_5$ |
| 42. | $-CH_2-(CH_2)_2-(CH_2)_2-$ | O | $-(CH_2)_4-$ | H | cyclopentyl-$CH_2$ | 4 | S | $C_6H_5-(CH_2)_2-$ |
| 43. | $-CH_2-(CH_2)_2-(CH_2)_4-$ | O | $-(CH_2)_3-$ | $C_2H_5$ | $C_4H_9\overset{O}{\overset{\|}{C}}$ | 2 | S | cyclopentyl |
| 44. | $-CH_2-(CH_2)_3-(CH_2)_3-$ | O | $-(CH_2)_2-$ | $C_3H_7$ | $C_6H_5-\overset{O}{\overset{\|}{C}}$ | 3 | S | cyclohexyl-$CH_2-$ |
| 45. | $-CH_2-CH=CH-(CH_2)_2-$ | S | $(CH_2)_2$ | $CH_3$ | $CH_3$ | 1 | S | $C_6H_5$ |
| 46. | $-CH_2-CH=CH-$ | S | $-CH_2\overset{CH_3}{\overset{\|}{CH}}-$ | $C_2H_5$ | H | 2 | S | $C_6H_5CH_2$ |
| 47. | $-CH_2-CH=CH-(CH_2)_3-$ | S | $-(CH_2)_3-$ | H | $C_2H_5$ | 2 | S | cyclohexyl |
| 48. | $-CH_2-CH=CH-(CH_2)_4-$ | S | $-(CH_2)_4-$ | $CH_3$ | $C_6H_5$ | 1 | S | cyclopentyl-$CH_2-$ |
| 49. | $-CH_2CH=CH-CH_2-$ | S | $-(CH_2)_2-$ | $C_2H_5$ | $CH_3$ | 3 | S | $CH_3CH_2CH=CH-CH_2-$ |
| 50. | $-CH_2-CH=CH-$ | S | $-(CH_2)_3-$ | H | H | 3 | S | $CH_3CH_2\equiv C-CH_2-$ |
| 51. | $-CH_2-(CH_2)_2-CH_2-$ | S | $(CH_2)_2-$ | $CH_3$ | $C_6H_5CH_2$ | 1 | S | $C_3H_7$ |
| 52. | $-CH_2-(CH_2)_2-$ | S | $-(CH_2)_3-$ | $CH_3$ | cyclohexyl | 2 | S | $C_6H_5$ |
| 53. | $-CH_2-(CH_2)_2-(CH_2)_2-$ | S | $-(CH_2)_4-$ | H | cyclopentyl-$CH_2$ | 4 | S | $C_6H_5-(CH_2)_2-$ |
| 54. | $-CH_2-(CH_2)_2-(CH_2)_4-$ | S | $-(CH_2)_3-$ | $C_2H_5$ | $CH_3\overset{O}{\overset{\|}{C}}-$ | 2 | S | cyclopentyl |
| 55. | $-CH_2-(CH_2)_3-(CH_2)_3-$ | S | $-(CH_2)_2-$ | $C_3H_7$ | $C_6H_5\overset{O}{\overset{\|}{C}}-$ | 3 | S | cyclohexyl-$CH_2-$ |

What is claimed is:

1. A compound of the structure

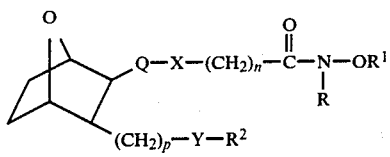

including all stereoisomers thereof, wherein Q is —CH$_2$—A—(CH$_2$)$_m$— wherein A is —CH=CH— or —(CH$_2$)$_2$—, m is 1 to 6 wherein A is CH=CH and m is 0 to 6 wherein A is (CH$_2$)$_2$; X is S or O; n is 1 to 4; R is H, lower alkyl, aryl, aralkyl or cycloalkyl; R$^1$ is H, lower alkyl, aryl, aralkyl, cycloalkyl, alkanoyl or aroyl; p is 1 to 5; Y is O or

wherein q is 0, 1 or 2; and R$^2$ is lower alkyl, aryl, aralalkyl, cycloalkyl, cycloalkylalkyl, lower alkenyl containing 2 to 12 carbons or lower alkynyl containing 2 to 12 carbons, wherein lower alkyl or alkyl alone or as part of another group contains 1 to 12 carbons and is unsubstituted or is substituted with halo, CF$_3$, alkoxy, aryl, alkyl-aryl, haloaryl, cycloalkyl, or alkylcycloalkyl;

aryl alone or as part of another group is phenyl or naphthyl which is unsubstituted or is substituted with 1 or 2 lower alkyl groups, 1 or 2 halogens and/or 1 or 2 lower alkoxy groups;

cycloalkyl alone or as part of another group contains 3 to 12 carbons and is unsubstituted or is substituted with 1 or 2 halogens, 1 or 2 lower alkyl groups and/or 1 or 2 lower alkoxy groups; and (CH$_2$)$_m$, (CH$_2$)$_n$ and (CH$_2$)$_p$ may independently contain 1 or 2 lower alkyl and/or halo substituents.

2. The compound as defined in claim 1 wherein X is O.

3. The compound as defined in claim 1 wherein X is S.

4. The compound as defined in claim 1 wherein p is 1.

5. The compound as defined in claim 1 wherein A is CH=CH.

6. The compound as defined in claim 1 wherein A is (CH$_2$)$_2$.

7. The compound as defined in claim 6 wherein m is 0.

8. The compound as defined in claim 1 wherein m is 1 to 3 and n is 1 to 3.

9. The compound as defined in claim 1 wherein Y is O.

10. The compound as defined in claim 1 wherein Y is S.

11. The compound as defined in claim 5 wherein A is CH$_2$—CH$_2$ or CH=CH, m is 1 to 3, n is 1 to 3, X is O, R$^1$ is H, R is lower alkyl, p is 1, Y is O or S and R$^2$ is lower alkyl, phenyl or benzyl.

12. The compound as defined in claim 1 wherein R$^2$ is butyl, pentyl, hexyl or heptyl including all isomers thereof.

13. The compound as defined in claim 1 having the name [1α,2β(2Z),3β,4α]-[[4-[3-[(hexyloxy)methyl-7-oxabicyclo[2.2.1]hept-2-yl]-2-butenyl]oxy]-N-hydroxy-N-methylacetamide including all stereoisomers thereof.

14. The compound as defined in claim 1 having the name [1α,2β,3β,4α]-2-[[4-[3-[(hexylthio)methyl]-7-oxabicyclo[2.2.1]hept-2-yl]butyl]oxy]-N-hydroxy-N-methylacetamide including all stereoisomers thereof.

15. The compound as defined in claim 1 having the name [1α,2β,3β,4α]-2-[[4-[3-[(hexyloxy)methyl]-7-oxabicyclo[2.2.1]hept-2-yl]butyl]oxy]-N-hydroxy-N,2,2-trimethylacetamide including all stereoisomers.

16. The compound as defined in claim 1 having the name [1α,2β(2Z),3β,4α]-2-[[4-[3-(hexyloxy)methyl]-7-oxabicyclo[2.2.1]hept-2-yl]-2-butenyl]oxy]-N-hydroxy-N,2,2-trimethyl acetamide including all stereoisomers thereof.

17. A composition for inhibiting allergic conditions in a mammalian species, comprising an effective amount of a compound as defined in claim 1 or a pharmaceutically acceptable salt thereof, and a pharmaceutically acceptable carrier thereof.

18. A method of inhibiting Δ$^5$-lipoxygenase which comprises administering to the circulatory system of a mammalian host an effective amount of a compound as defined in claim 1 or a pharmaceutically acceptable salt thereof.

19. The method as defined in claim 18 wherein said compound is administered in an amount within the range of from about 1 to about 100 mg/kg.

20. A method for treating asthma, inhibiting or reducing inflammation or inhibiting or treating psoriasis, in a mammalian species in need of such treatment, which comprises administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,654,367
DATED : March 31, 1987
INVENTOR(S) : Ravi K. Varma et al.

It is certified that error appears in the above-identified patent and that said Letters Patent is hereby corrected as shown below:

Column 45, line 23, "aralal-" should read --arylal- --.

Signed and Sealed this

Twenty-second Day of December, 1987

Attest:

DONALD J. QUIGG

Attesting Officer     Commissioner of Patents and Trademarks